(12) United States Patent
Schwer

(10) Patent No.: US 7,566,302 B2
(45) Date of Patent: Jul. 28, 2009

(54) EXPANDABLE ACCESS DEVICE

(75) Inventor: Stefan Schwer, Loerrach (DE)

(73) Assignee: Synthes USA, LLC, West Chester, PA (US)

( * ) Notice: Subject to any disclaimer, the term of this patent is extended or adjusted under 35 U.S.C. 154(b) by 365 days.

(21) Appl. No.: 11/193,807

(22) Filed: Jul. 28, 2005

(65) Prior Publication Data
US 2007/0027364 A1    Feb. 1, 2007

(51) Int. Cl.
*A61B 1/32*    (2006.01)
(52) U.S. Cl. ..................................................... 600/219
(58) Field of Classification Search ............... 600/219, 600/220, 222, 225, 201, 218, 184, 190, 197; 606/105
See application file for complete search history.

(56) References Cited

U.S. PATENT DOCUMENTS

| | | | | |
|---|---|---|---|---|
| 3,702,606 A | * | 11/1972 | Barnard | 600/220 |
| 5,514,153 A | | 5/1996 | Bonutti | 606/190 |
| 5,569,300 A | * | 10/1996 | Redmon | 606/207 |
| 5,681,265 A | | 10/1997 | Maeda | 600/219 |
| 5,728,046 A | | 3/1998 | Mayer | 600/210 |
| 5,827,314 A | * | 10/1998 | Lunsford et al. | 606/192 |
| 5,951,466 A | | 9/1999 | Segermark | 600/225 |
| 5,954,635 A | | 9/1999 | Foley | 600/114 |
| 6,187,000 B1 | | 2/2001 | Davison | 606/1 |
| 6,235,028 B1 | | 5/2001 | Brumfield | 606/53 |
| 6,302,842 B1 | * | 10/2001 | Auerbach et al. | 600/220 |
| 6,309,349 B1 | | 10/2001 | Bertolero | 600/213 |
| 6,520,907 B1 | | 2/2003 | Foley | 600/114 |
| 6,530,926 B1 | | 3/2003 | Davison | 606/61 |
| 6,575,899 B1 | | 6/2003 | Foley | 600/114 |
| 6,652,553 B2 | | 11/2003 | Davison | 606/190 |
| 6,712,795 B1 | | 3/2004 | Cohen | 604/233 |
| 6,716,218 B2 | * | 4/2004 | Holmes et al. | 606/105 |
| 6,746,396 B1 | | 6/2004 | Herman et al. | 600/233 |
| 6,800,084 B2 | | 10/2004 | Davison | 606/198 |

(Continued)

FOREIGN PATENT DOCUMENTS

DE        203 20 501        11/2004

(Continued)

*Primary Examiner*—Cris L Rodriguez
*Assistant Examiner*—Sunil K Singh
(74) *Attorney, Agent, or Firm*—Stroock & Stroock & Lavan LLP

(57) ABSTRACT

An expandable access device for providing access to a surgical site in the body. The expandable access device comprises a first blade, a second blade and a connection mechanism operable connecting the first and second blades. Each blade may have a first portion, a second portion and an intermediate portion between the first and second portions. The intermediate portions of each blade may be bent such that the first and second portions of each blade may be at an angle with respect to each other. The connection mechanism may have first and second elongated member, which may be in a criss-cross configuration. A first end of the first and second elongated members may be connected to the first blade and a second end of the first and second elongated members may be connected to the second blade. Such a construction may enable the first and second blades to separate and pivot with respect to each other. An actuating device may be connected to the first and second blades and/or the connecting mechanism and may be used to move the first and second blades with respect to each other.

14 Claims, 14 Drawing Sheets

U.S. PATENT DOCUMENTS

| | | | |
|---|---|---|---|
| 6,811,558 B2 | 11/2004 | Davison | 606/190 |
| 6,945,933 B2 | 9/2005 | Branch | 600/210 |
| 7,014,608 B2 | 3/2006 | Larson | 600/201 |
| 7,033,369 B2 | 4/2006 | Davison | 606/108 |
| 7,056,321 B2 | 6/2006 | Pagliuca | 606/61 |
| 7,144,368 B2 * | 12/2006 | Larson et al. | 600/215 |
| 7,144,393 B2 | 12/2006 | DiPoto | 606/1 |
| 7,179,225 B2 * | 2/2007 | Shluzas et al. | 600/219 |
| 7,182,729 B2 | 2/2007 | Abdelgany | 600/219 |
| 7,198,598 B2 | 4/2007 | Smith | 600/114 |
| 7,210,485 B2 * | 5/2007 | Zinkel | 128/898 |
| 7,261,688 B2 | 8/2007 | Smith | 600/210 |
| 2003/0073998 A1 | 4/2003 | Pagliuca | 606/61 |
| 2003/0139648 A1 | 7/2003 | Foley | 600/114 |
| 2003/0149341 A1 | 8/2003 | Clifton | 600/210 |
| 2003/0199871 A1 | 10/2003 | Foley | 606/54 |
| 2003/0225416 A1 * | 12/2003 | Bonvallet et al. | 606/105 |
| 2004/0034351 A1 | 2/2004 | Sherman | 606/61 |
| 2004/0059339 A1 | 3/2004 | Roehm | 606/90 |
| 2004/0116777 A1 | 6/2004 | Larson | 600/210 |
| 2004/0133201 A1 | 7/2004 | Shluzas | 606/61 |
| 2004/0176763 A1 | 9/2004 | Foley | 606/60 |
| 2004/0230100 A1 | 11/2004 | Shluzas | 600/208 |
| 2004/0236317 A1 | 11/2004 | Davison | 606/1 |
| 2004/0236331 A1 | 11/2004 | Michelson | 606/61 |
| 2005/0033297 A1 | 2/2005 | Davison | 606/61 |
| 2005/0043754 A1 | 2/2005 | Davison | 606/198 |
| 2005/0080320 A1 | 4/2005 | Lee | 600/214 |
| 2005/0090824 A1 | 4/2005 | Shluzas | 606/61 |
| 2005/0090899 A1 | 4/2005 | DiPoto | 623/17.11 |
| 2005/0119665 A1 | 6/2005 | Keller | 606/99 |
| 2006/0004380 A1 * | 1/2006 | DiDomenico et al. | 606/105 |
| 2006/0155170 A1 | 7/2006 | Hanson | 600/201 |
| 2006/0235279 A1 * | 10/2006 | Hawkes et al. | 600/222 |

FOREIGN PATENT DOCUMENTS

| | | |
|---|---|---|
| GB | 287 529 | 3/1927 |
| WO | WO 2004/062489 | 7/2004 |

* cited by examiner

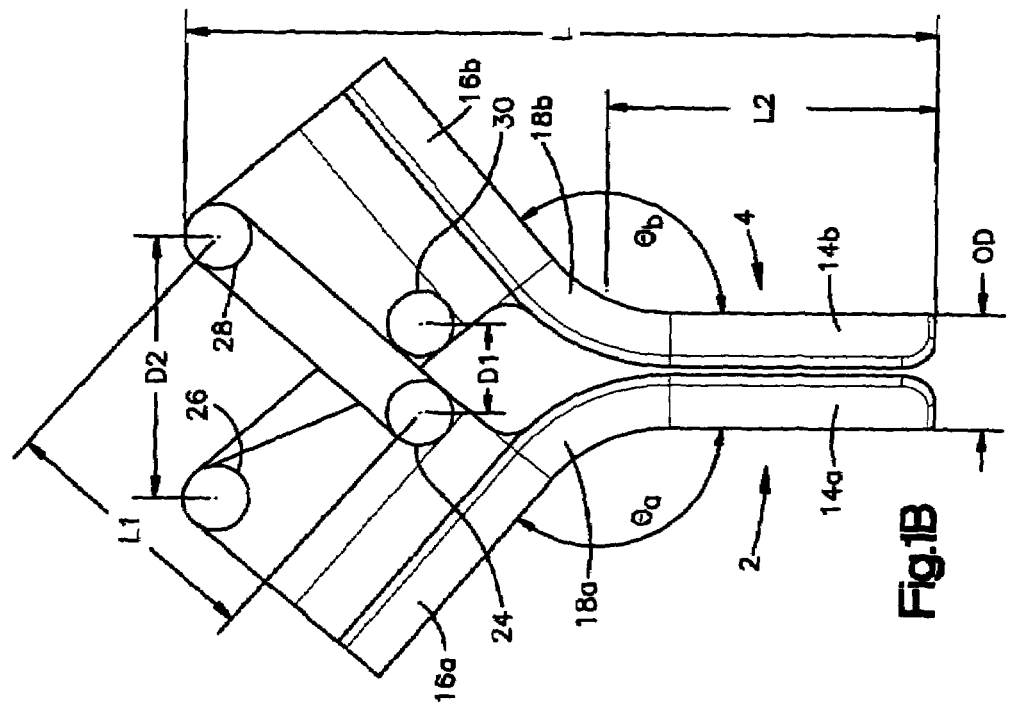
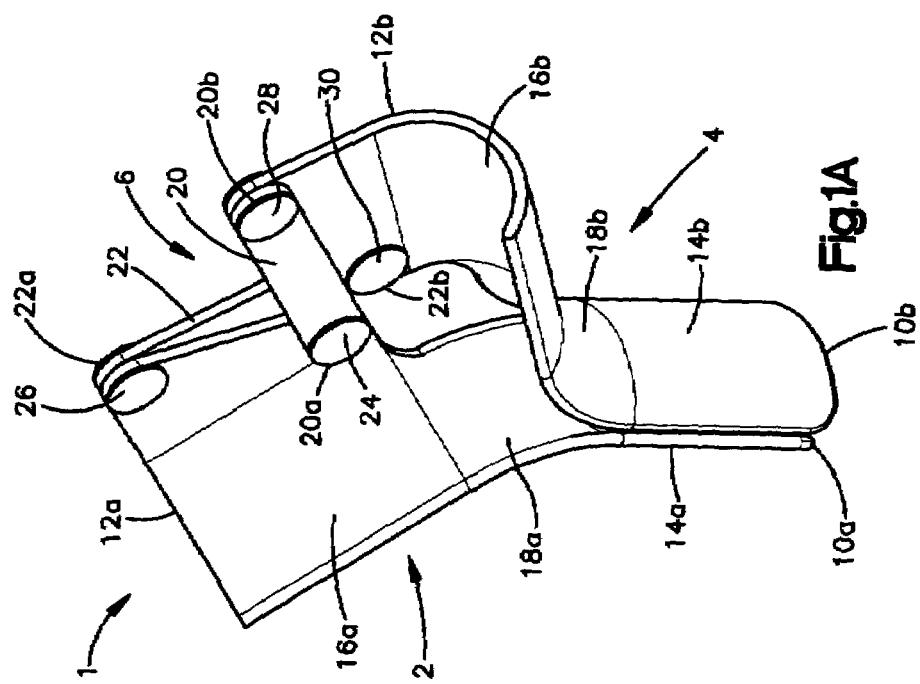

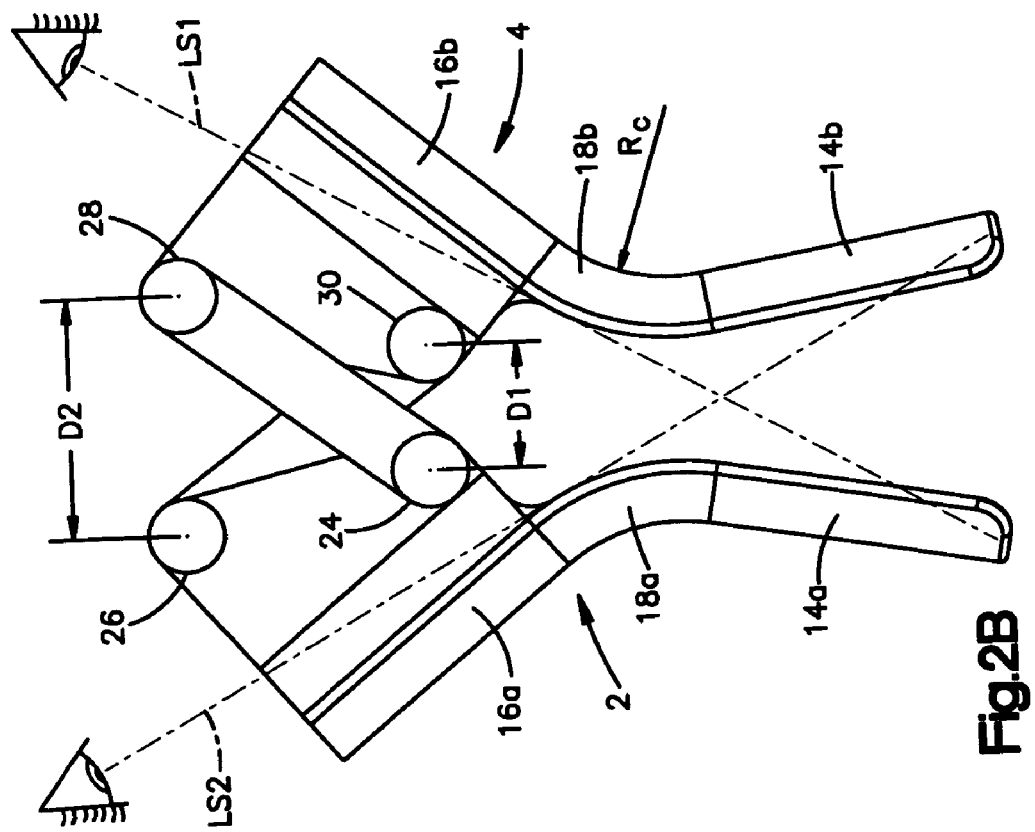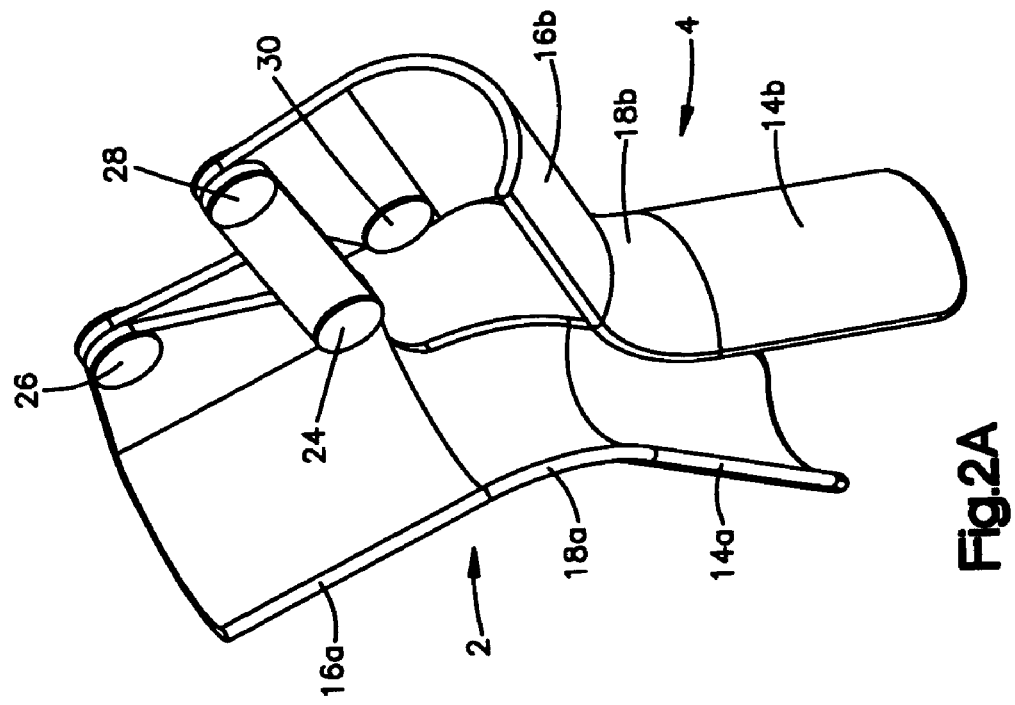

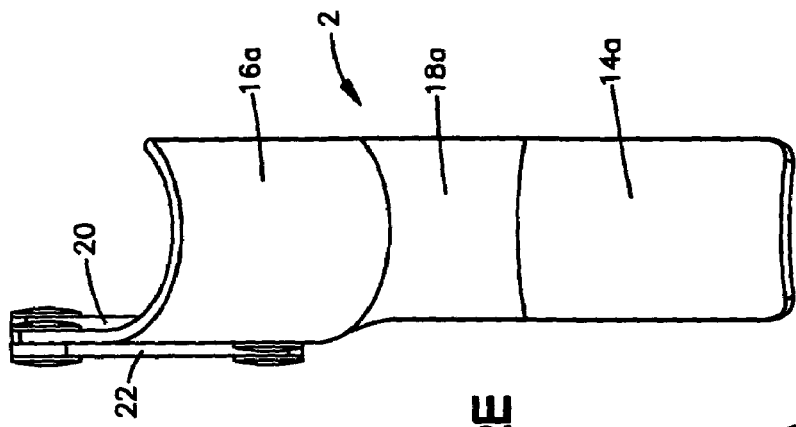
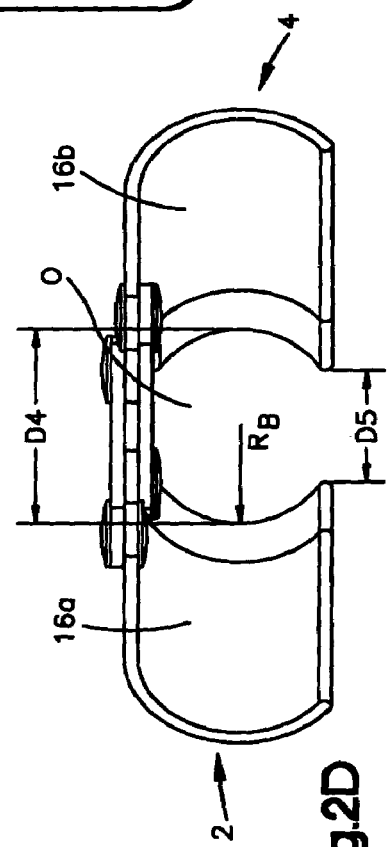
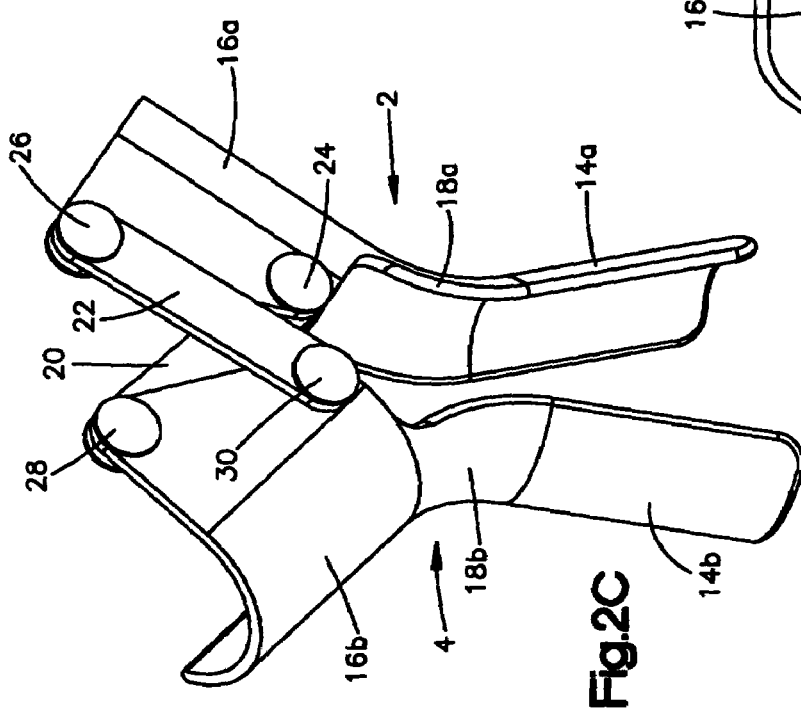

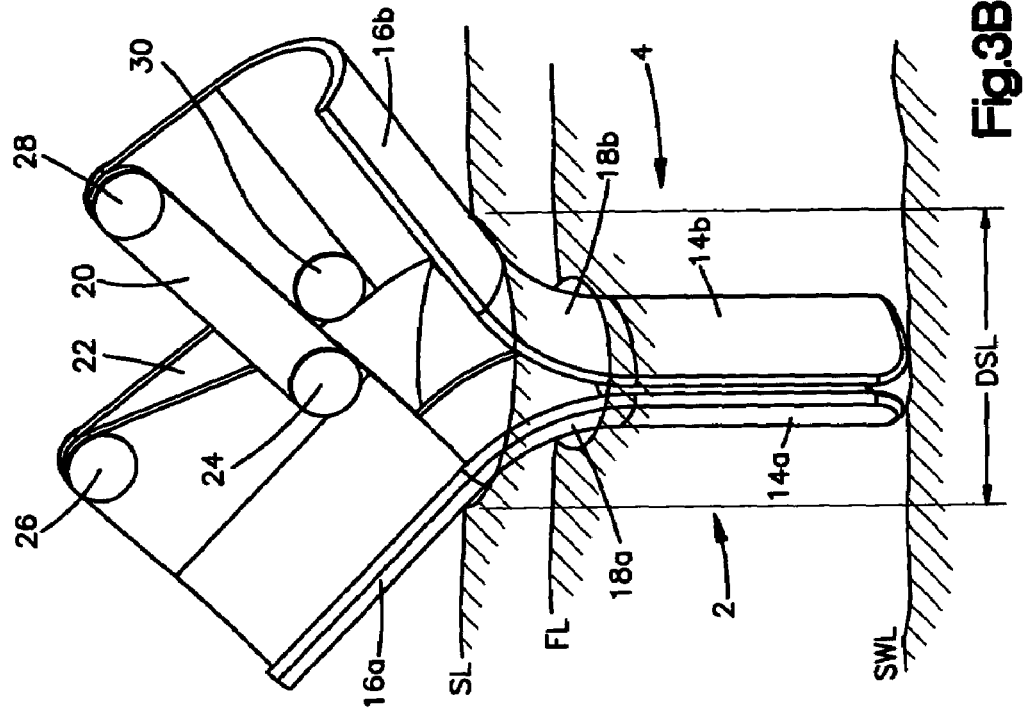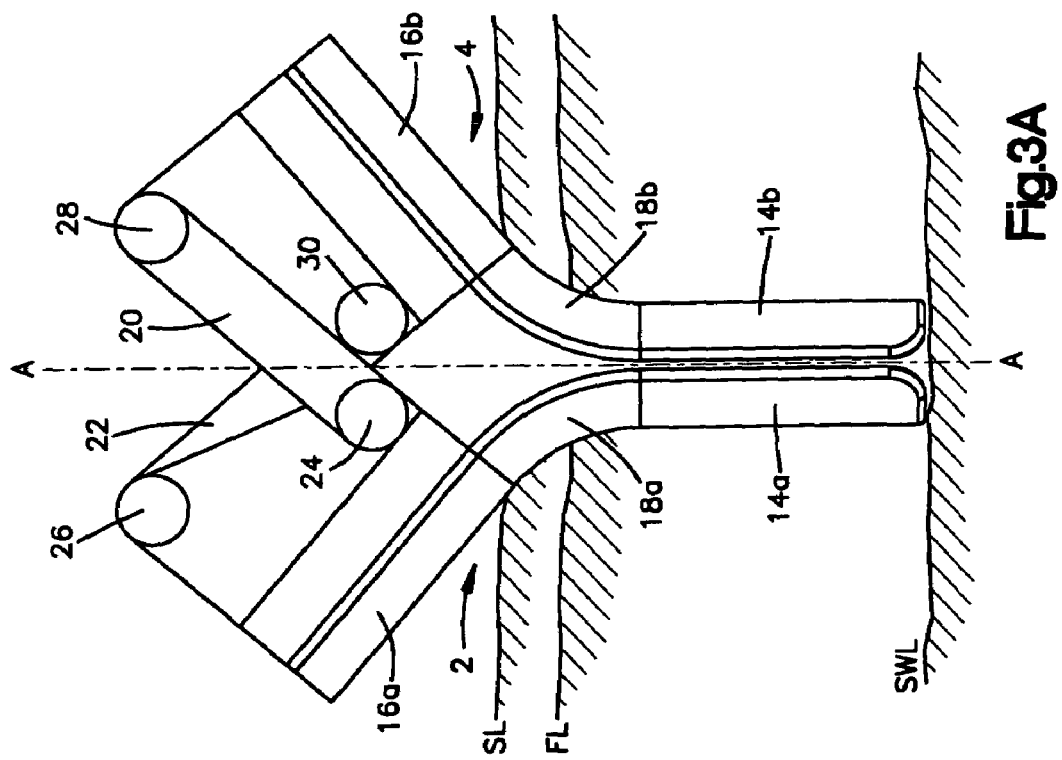

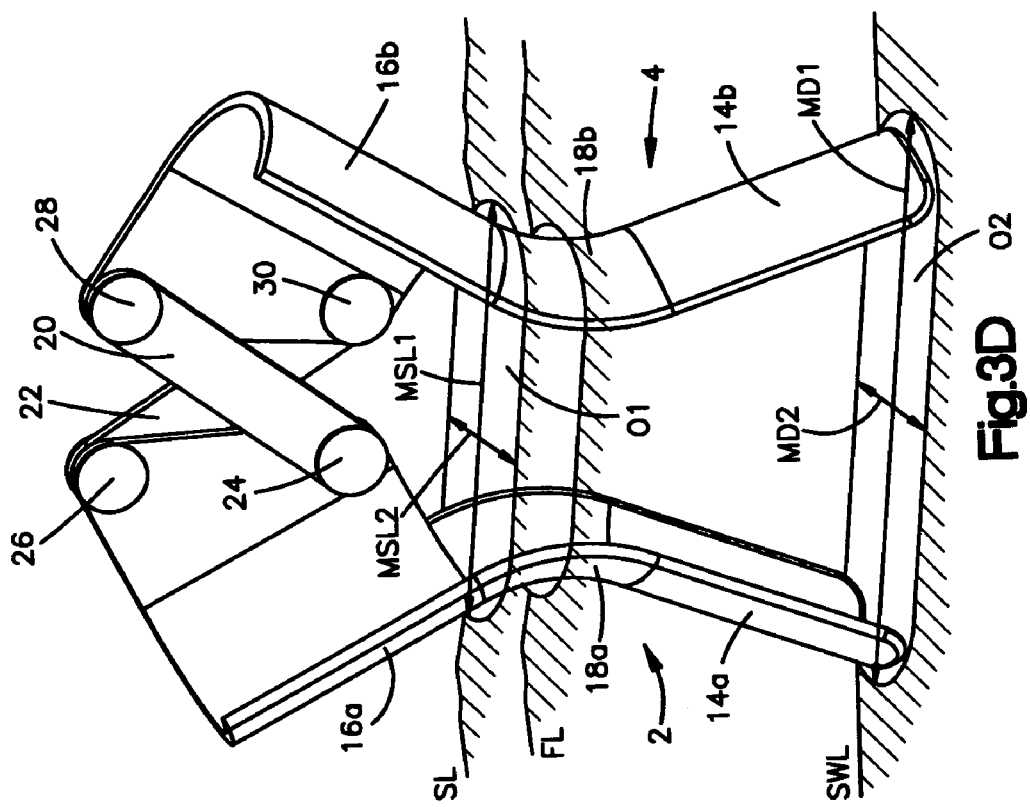
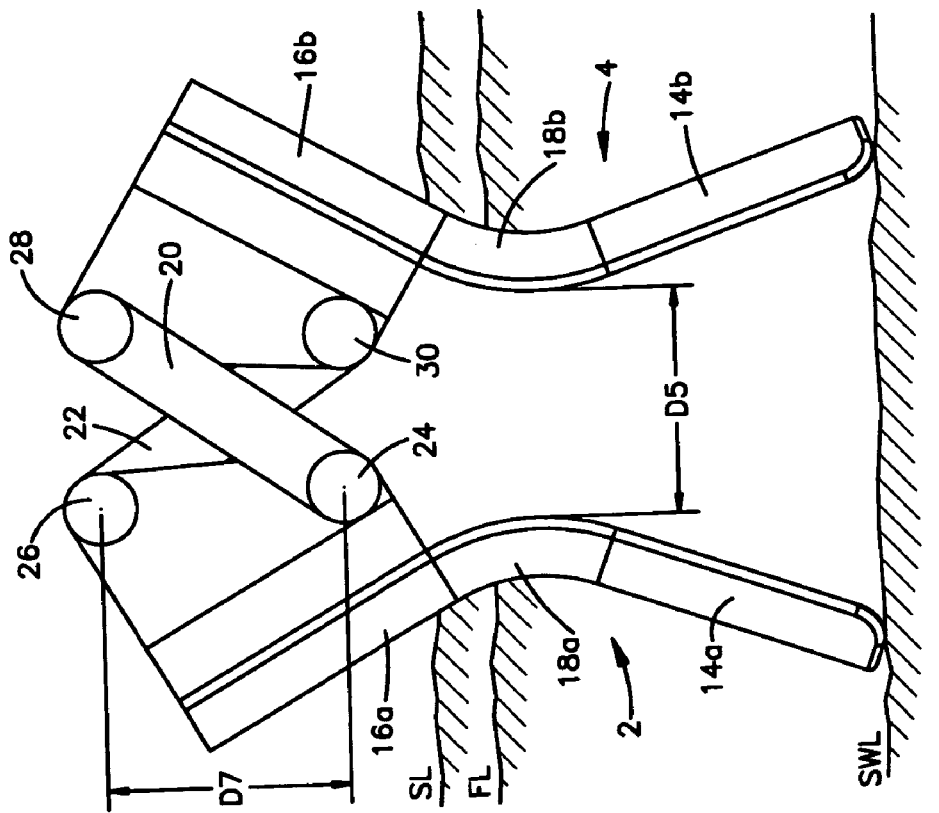

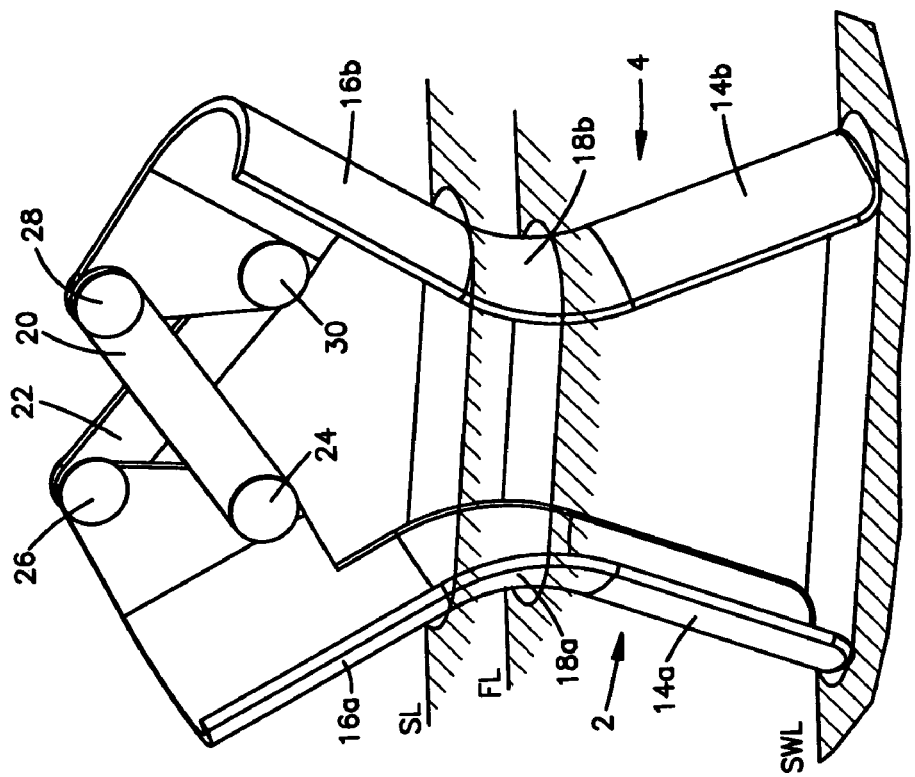
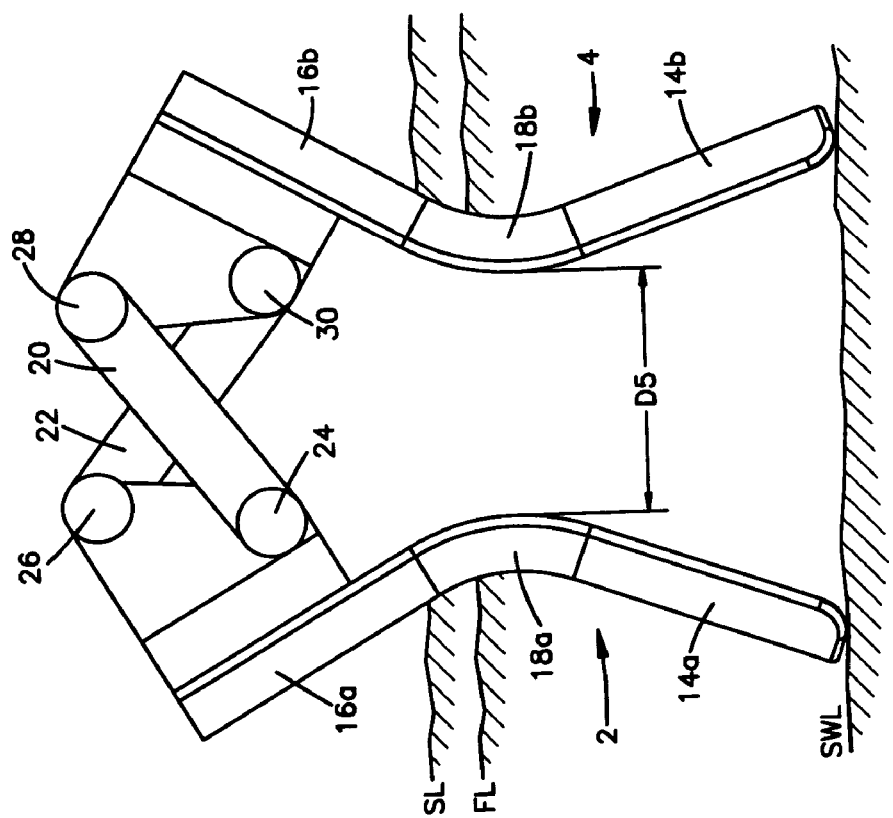

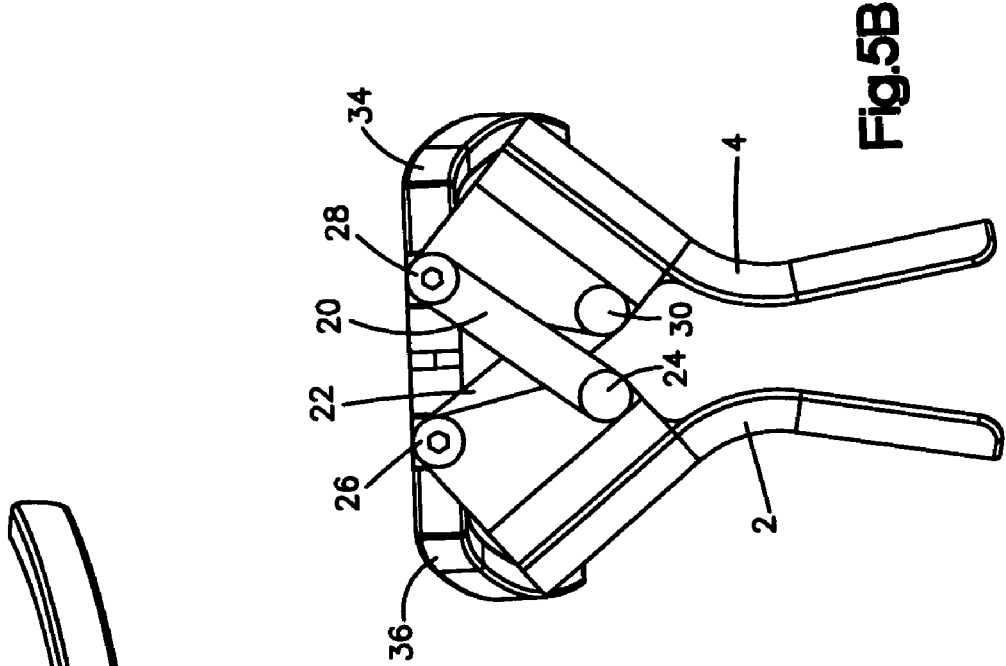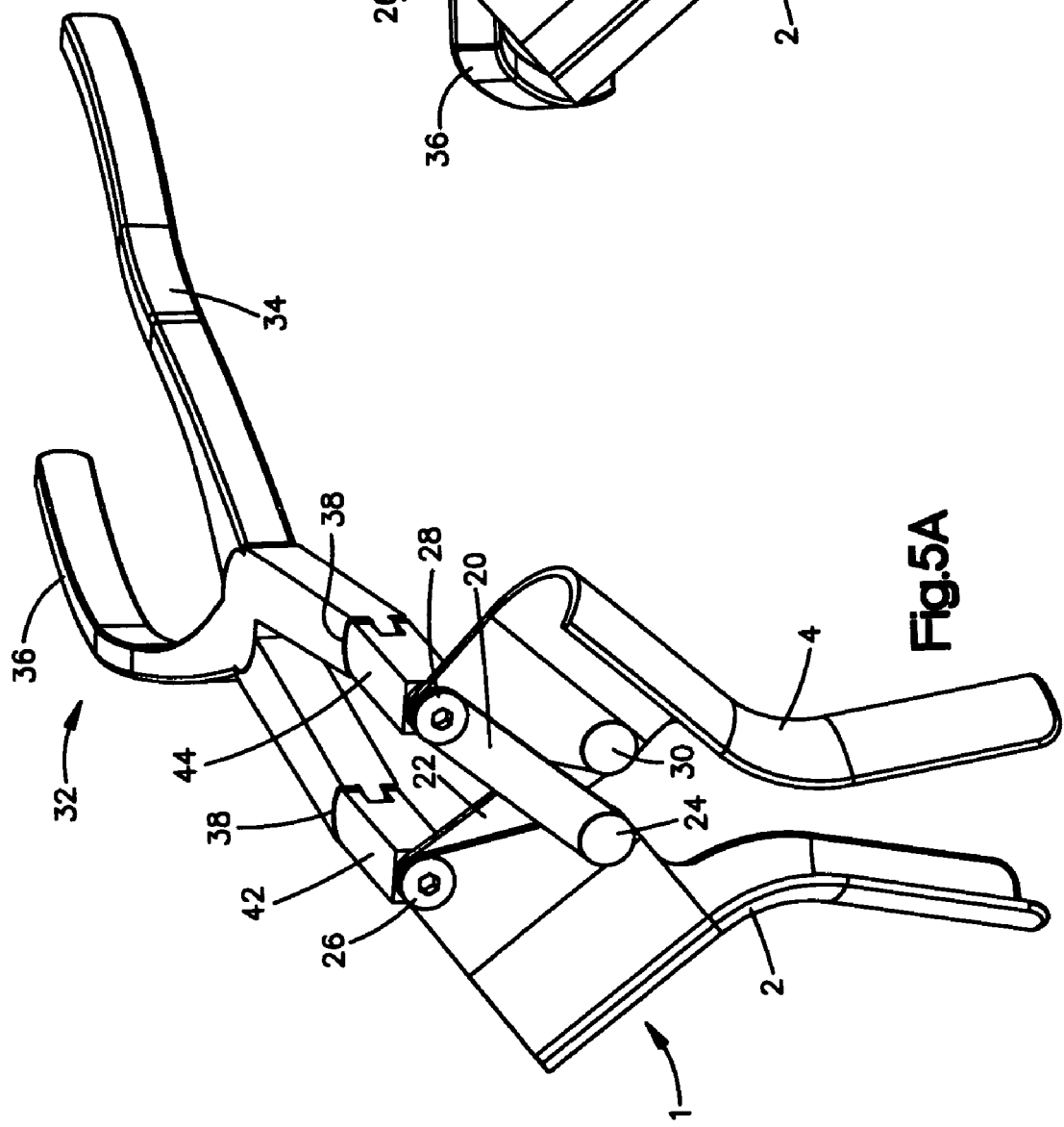

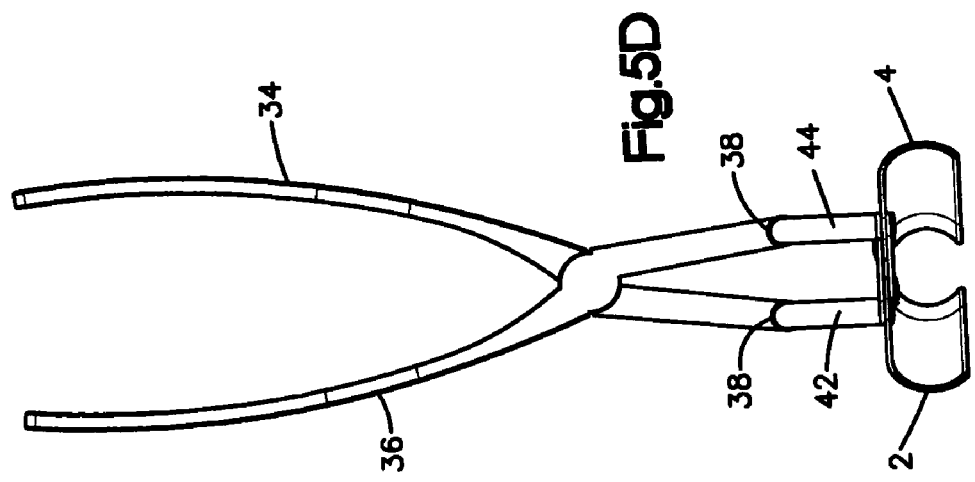
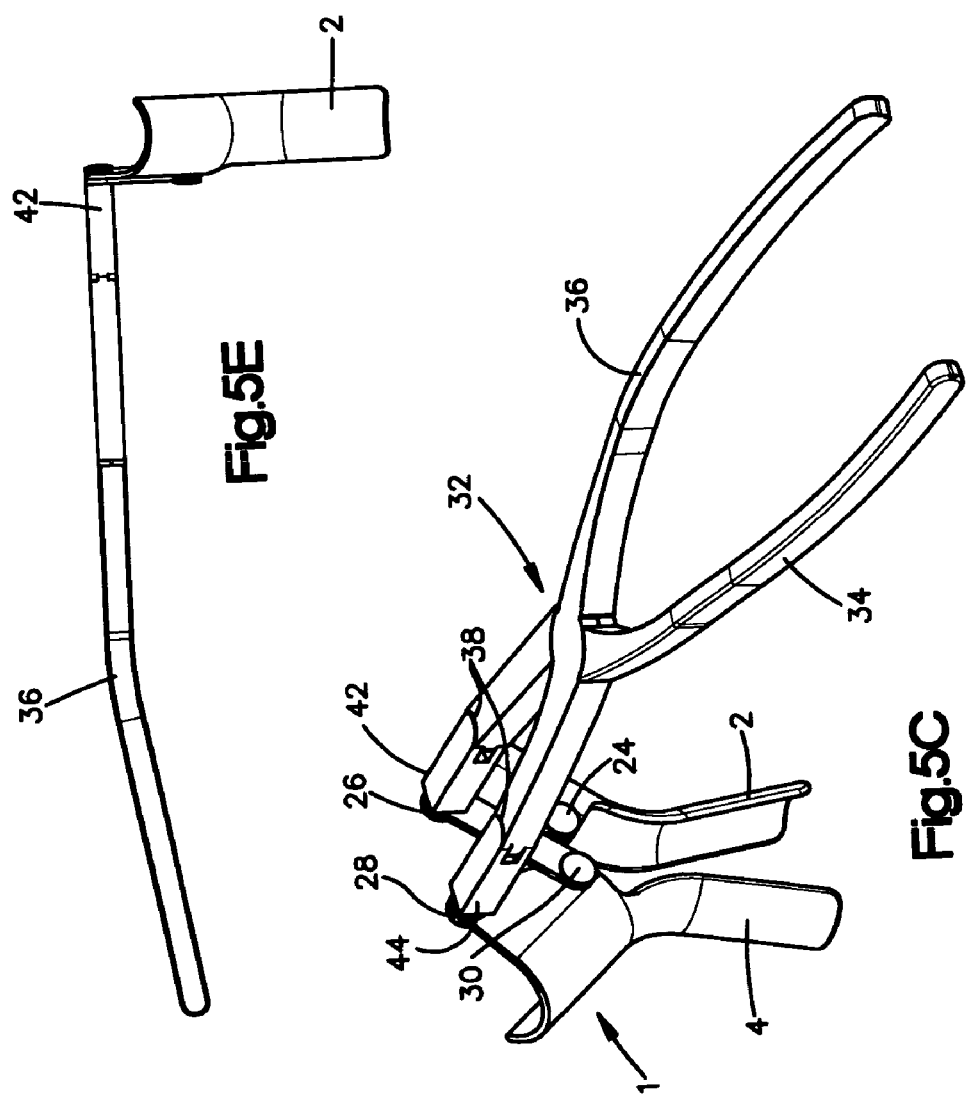

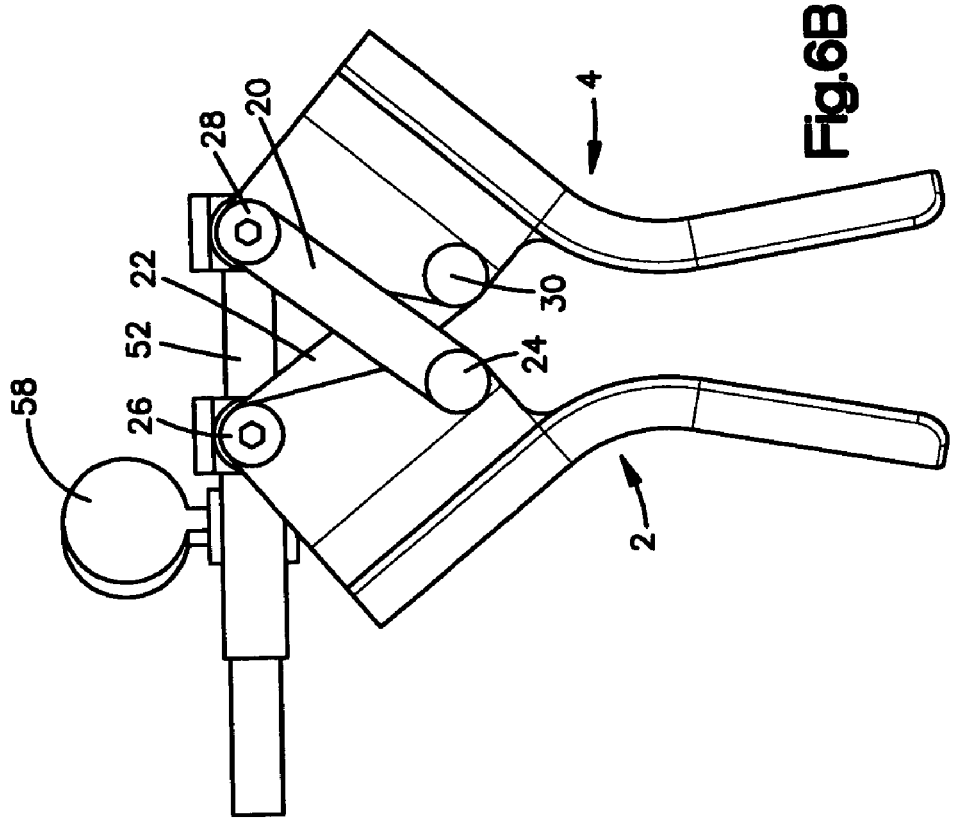
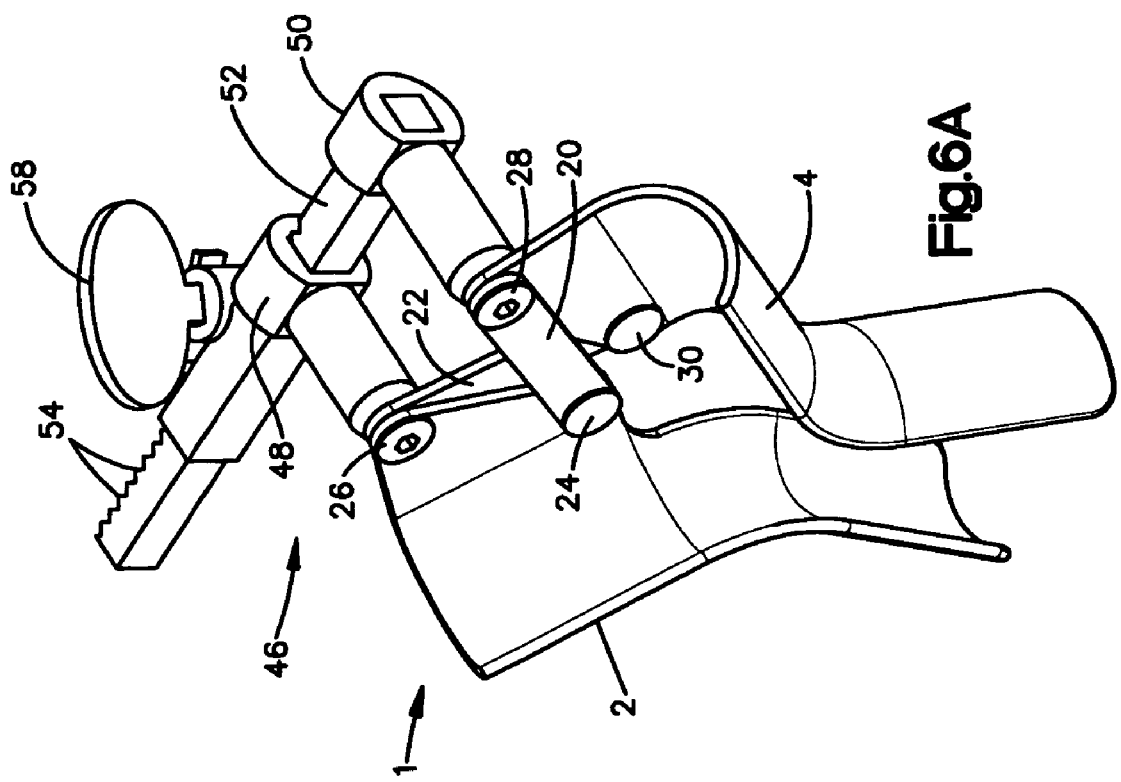

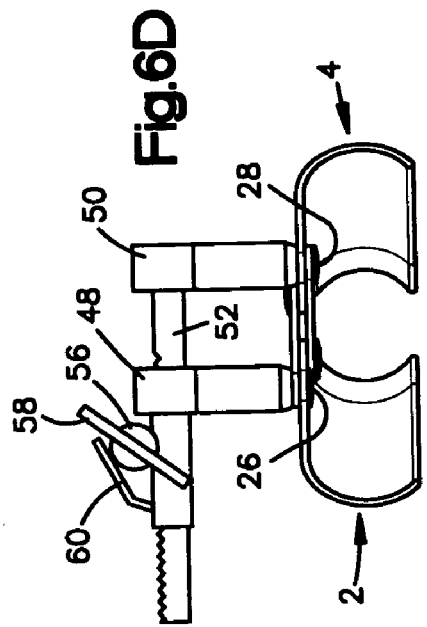
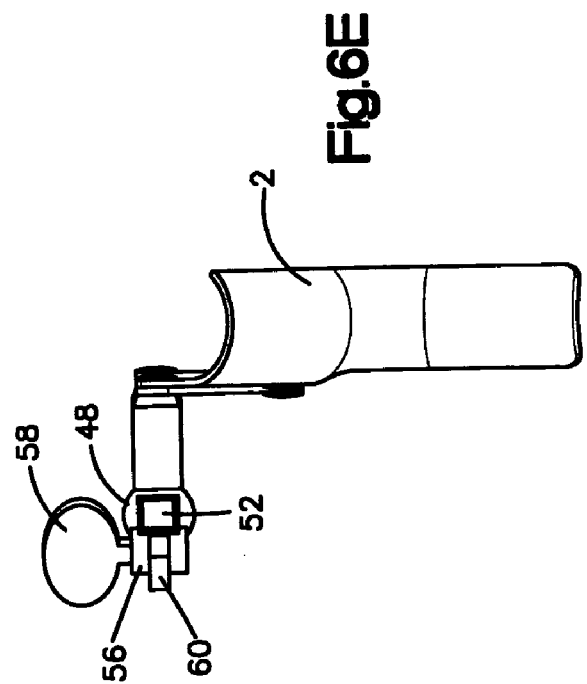
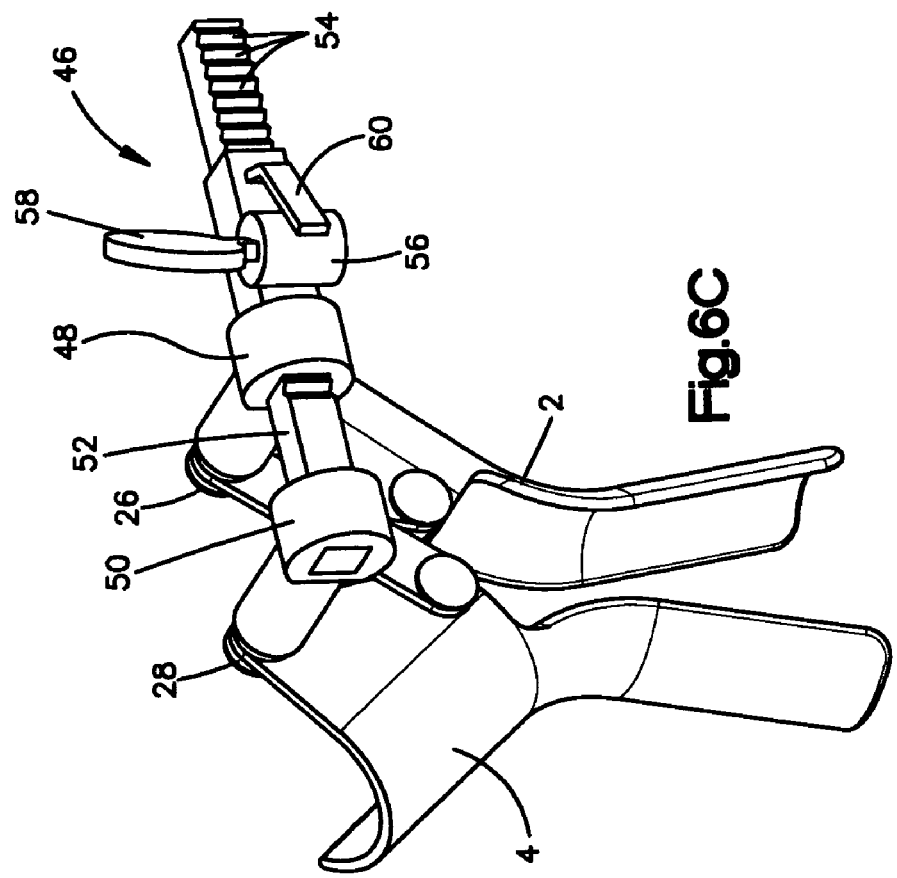

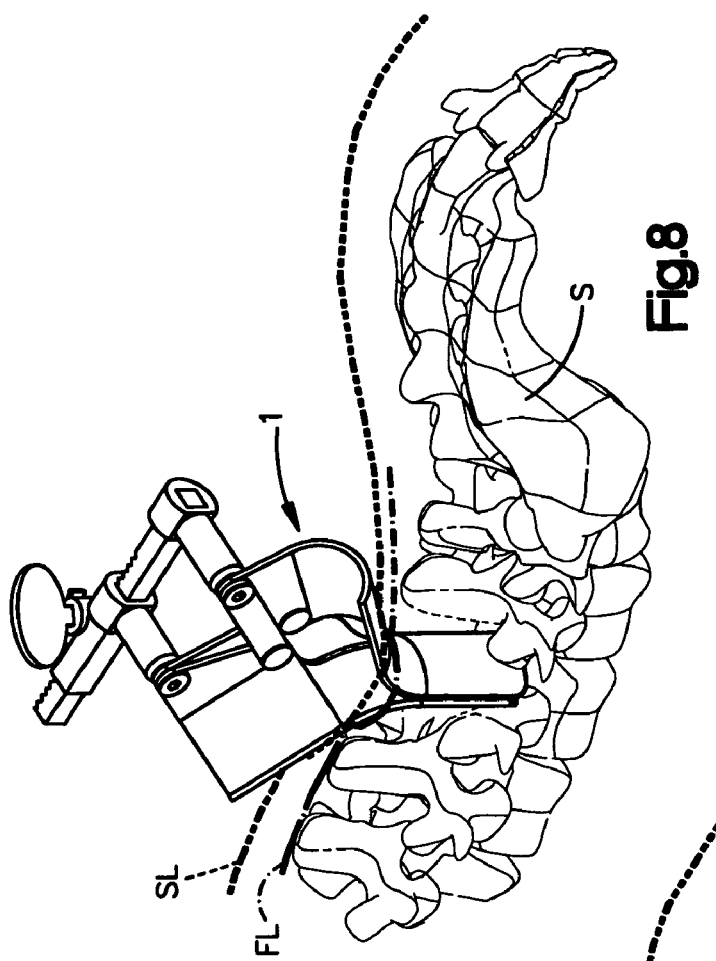
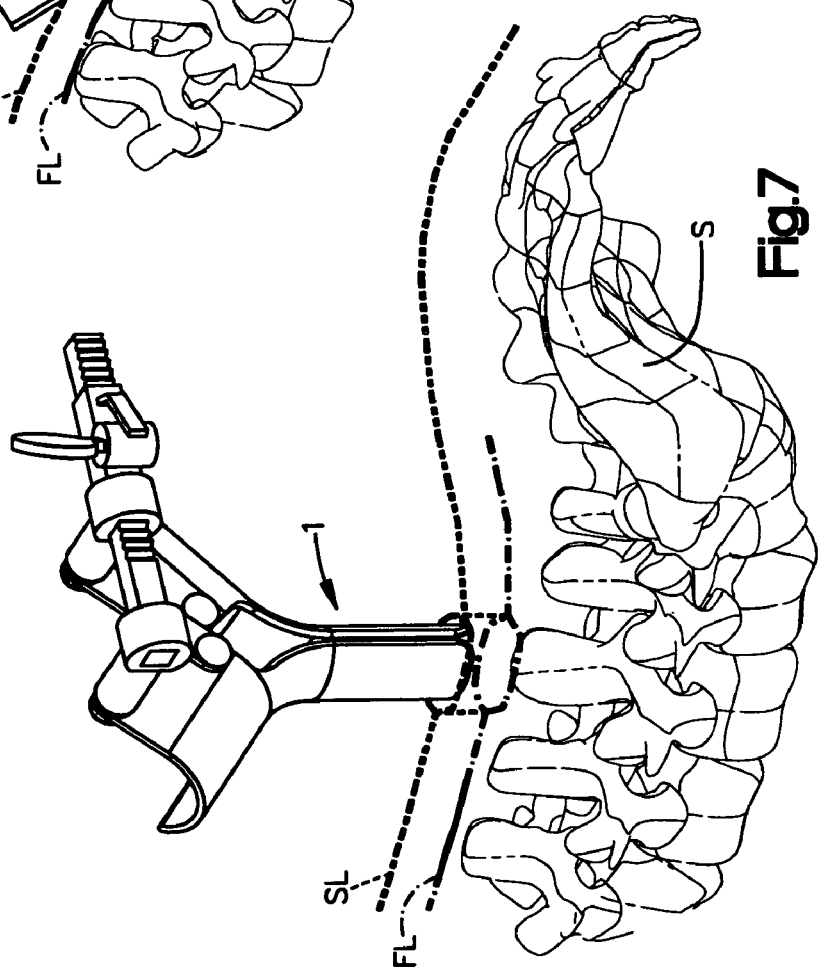

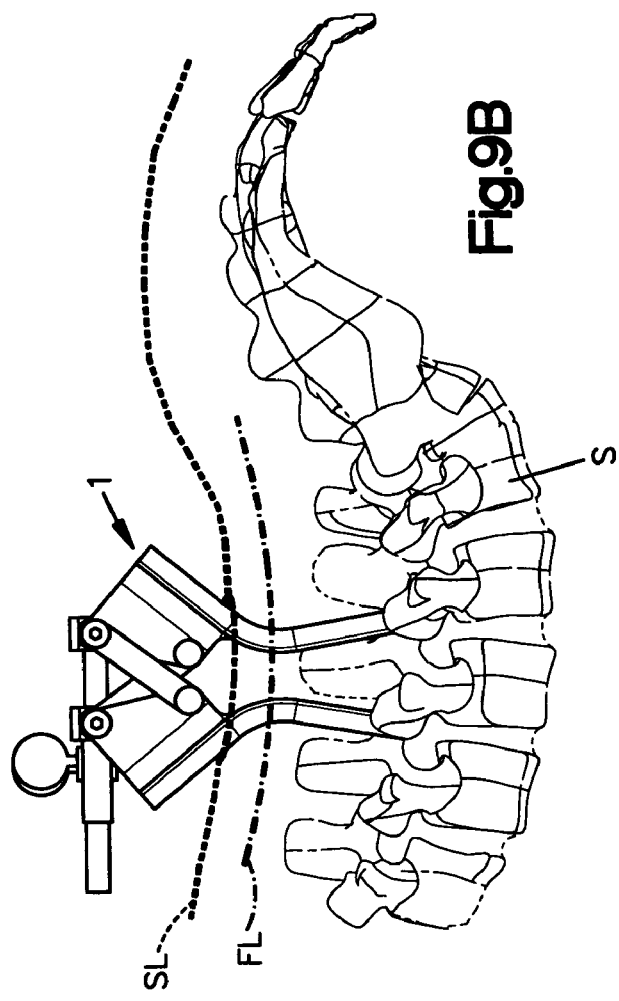
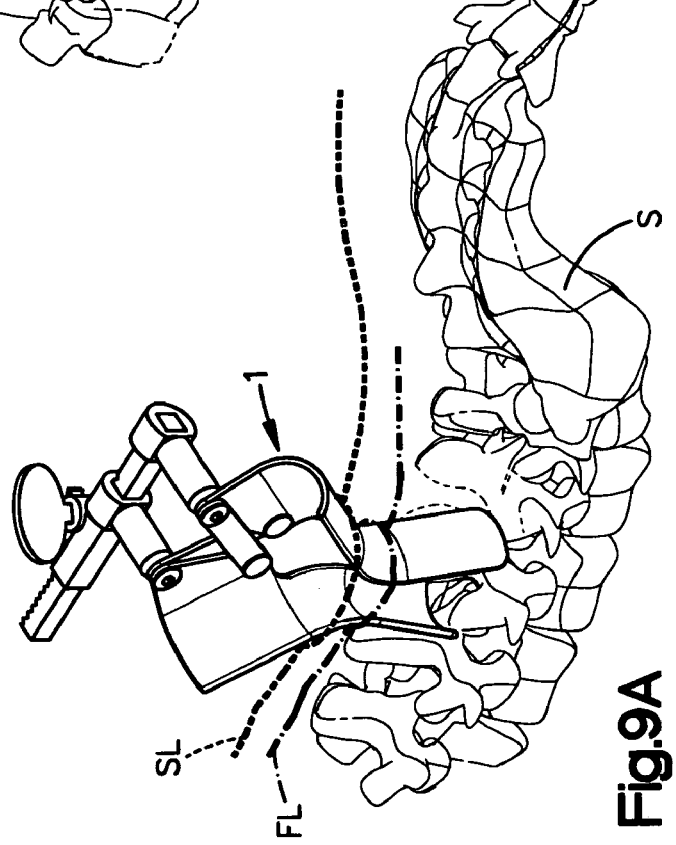
Fig.9B
Fig.9A

EXPANDABLE ACCESS DEVICE

FIELD OF THE INVENTION

The present invention relates to a device and method for providing access to a surgical site in the body and, more particularly, to an expandable access device and its method of use. The device may have applicability to, for example, minimally invasive surgery including, for example, surgery on the spine or other locations in the body.

BACKGROUND OF THE INVENTION

Retractors have been used in surgical procedures to provide access to a surgical site in the body. These retractors enable a surgeon to visualize a surgical site as well as enable a surgeon to insert tools into the body to perform a surgical procedure. One type of retractor has two or more blades which are spread apart generally parallel to each other to create an opening. These retractors require relatively large incisions and result in tissue being uniformly stretched or dissected from the exterior of the body at the skin down to a surgical site. Such a retractor may result in significant trauma to the body and may necessitate long recovery time.

Other types of retractors have blades which are pivotable with respect to each other. Such a construction allows the blades to be opened at an angle with respect to each other and requires a smaller skin incision than parallel spreading retractors. The use of pivotable retractors results in tissue proximate the skin level being stretched less than tissue at the surgical site. These retractors may be useful, for example, for pedicle screw fixation where the trajectories of the pedicle screws, viewed from the side of the body, converge due to the natural lordosis in the lumbar spine. This convergence may necessitate a shorter skin incision compared to the opening that needs to be created directly above the lamina and the pedicles.

Furthermore, some retractors have portions which may be expanded inside the body to provide access to a surgical site. Pivotable and expandable retractors often require separate and/or complex mechanisms to control the spreading of the blades and/or expansion of the retractor. Therefore, it is desirable to have a device for providing access into the body which requires only a small skin incision, causes the least amount of trauma to the body and, at the same time, is relatively simple to operate.

SUMMARY OF THE INVENTION

The expandable access device described herein may include a first blade and a second blade joined by a connection mechanism. Each blade may have a length, a distal end, a proximal end, a first portion positioned proximate the distal end, a second portion positioned proximate the proximal end, and an intermediate portion, which may be located between the first and second portions. In one embodiment, the blades may be non-straight. For example, the intermediate portion may be bent or curved such that the first and/or second portions may be angled with respect to each other. Furthermore, the expandable access device may have a first or closed configuration, where the first portions of the blades are adjacent and/or parallel to each other. In the first or closed configuration, the second portions of the blades may be spaced apart and/or at an angle with respect to each other. The device may also have a second or opened configuration, where the first portions of the blades are spaced apart and/or at an angle with respect to each other.

The connection mechanism may be connected to the second portion of each blade and may be sized and configured to cause the blades to move towards or away from each other as well as pivot (e.g., angulate) with respect to each other. In a preferred embodiment, the connection mechanism may be made of a pair of elongated members (e.g., plates, bars) having first and second ends. The elongated members may be any shape such as, for example, flat or round. The first end of each elongated member may be attached to the first blade and the second end of each elongated member may be attached to the second blade. In a preferred embodiment, the first and second elongated members may be oriented in a criss-cross configuration.

Moreover, an actuating device may be attached to the connection mechanism and/or the blades and may be used to operate the connection mechanism. In a preferred embodiment, the actuating device may be any device which creates linear movement. The combination of the connection mechanism and a device which may impart linear movement may result in the first and second blades moving apart from each other while, at the same time, pivoting (e.g., angulate) with respect to each other. In one embodiment, the actuating device may be a pair of handles which may be operated in a scissor-type manner. In another embodiment, the actuating device may be a ratchet mechanism. The actuating device may be configured to be detachable from at least one of the first and second blades.

In one embodiment, the expandable access device may comprise a first blade which may have a distal end and proximal end; a second blade which may have a distal end and a proximal end, the second blade may be operably connected to the first blade. The device may also have a first elongated member which may have a first end and a second end, wherein the first end may be connected to the first blade at a first pivot point and the second end may be connected to the second blade at a second pivot point; and a second elongated member which may have a first end and a second end, wherein the first end may be connected to the first blade at a third pivot point and the second end may be connected to the second blade at a fourth pivot point. The distal end of the first blade may be moveable with respect to the distal end of the second blade.

The first blade may comprise a first portion, a second portion and an intermediate portion in between the first and second portion, wherein the first and second portions may be at an angle with respect to each other. The second blade may comprise a first portion, a second portion and an intermediate portion in between the first and second portion of the second blade, wherein the first and second portions of the second blade may be at an angle with respect to each other. The intermediate portion may be bent such that the first and second portions may be angled with respect to each other. Moreover, the intermediate portion of the second blade may be bent such that the first and second portions of the second blade may be angled with respect to each other. The device may have an opened configuration and closed configuration, wherein the intermediate portions of the first and second blades may be closer to each other than the distal most ends of the first and second blades when the device may be in the opened configuration.

The expandable access device may further include an actuating device operable connected to the first and second blades. The actuating mechanism may be operable connected to the proximal end of the first and second blades. For example, the actuating device may be operable connected to the first blade at the third pivot point and the second blade at the second pivot point. Furthermore, the first and second elongated members may form a connection mechanism. In one embodiment, the second pivot point of the device may be proximal the first pivot point and the fourth pivot point may be distal the third pivot point such that the first and second elongated members may be in a criss-cross configuration.

In another embodiment, the expandable access device may have a first blade with a distal end and proximal end; a second blade with a distal end and a proximal end, wherein the second blade may be operably connected to the first blade; a connection mechanism which may be operably connected to the first and second blades, wherein the connection mechanism may be sized and configured so that the first and second blades may separate and pivot with respect to each other; and an actuating device which may move the first and second blades relative to each other. The first blade may comprise a first portion, a second portion and an intermediate portion in between the first and second portion, wherein the first and second portion of the first blade may be at an angle with respect to each other, and wherein the second blade may comprise a first portion, a second portion and an intermediate portion in between the first and second portion of the second blade, wherein the first and second portion of the second blade may be at an angle with respect to each other. In some embodiments, the first and second blades may have an inner and outer surface, wherein the inner surface may be concave and the outer surface may be convex. The device may have an opened and closed configuration, wherein the intermediate portions of the first and second blades may be closer to each other than the distal most ends of the first and second blades when the device is in the opened configuration.

In yet another embodiment, the device may include a first blade which may have a distal end and a proximal end, the distal end may have a distal portion associated therewith and the proximal end may have a proximal portion associated therewith, the proximal portion may be angled with respect to the distal portion; and a second blade which may have a distal end and a proximal end, the distal end may have a distal portion associated therewith and the proximal end may have a proximal portion associated therewith, the proximal portion may be angled with respect to the distal portion; wherein the first blade may be operably connected to the second blade such that, in a closed position, the distal ends of the first ands second blades may be adjacent each other while the proximal ends of the first and second portions may be space apart and, in an open position, the proximal ends of the first and second blades may be closer together than in the closed position and the distal ends of the first and second blades may be farther apart than in the closed position.

In use, the blades may be inserted in the first or closed configuration through an incision in the skin. For example, the blades may be inserted into the body until the intermediate portion of the blades may be positioned in and/or proximate the facia and/or skin incision. Once the blades are positioned at a desired depth in the body, a surgeon may move the actuating device so that the blades move apart and pivot with respect to each other to spread tissue. Thereafter, a surgical procedure may be performed through the expandable access device. Once the procedure is complete, a surgeon may move the actuating device so that the blades move towards each other and, in particular, the first portions of the blades may be positioned adjacent each other. The expandable access device may then be removed from the body.

The retractor is particularly useful, for example, to perform pedicle screw fixation or some other procedure on the spine. In one method, a Wiltse approach may be used to insert the device. A surgeon may make an incision in a patient's back (e.g., posterior, posterio-lateral, or lateral approach) which may be substantially perpendicular to and a distance from the spine (e.g., parallel to muscle fibers). The surgeon may then insert his/her finger or dilation device through the incision and into the underlying tissue to create cleavage or space between tissue sections (e.g., between the multifidus and the longisimus muscle). Thereafter, a surgeon may insert the first portion of the blades of the device into the space created by the surgeon in the closed configuration so that the width of the blades may be parallel to the spine. The surgeon may rotate the device (e.g., rotation of 90 degrees) such that the width of each blade may be at an angle (e.g., perpendicular) to the spine. A surgeon may then operate the actuating device to move the blades apart and pivot the blades with respect to each other. Such a construction may result in the opening in the facia and/or skin having a smaller dimension than the opening proximate the vertebrae.

One method of inserting the expandable access device into the body may include providing an expandable device such as those described above, inserting the blades into the body such the distal ends of the blades may be positioned adjacent a surgical work site, and moving the blades between an opened and closed position, wherein, in the closed position, the distal ends of the first and second blades may be adjacent each other while the proximal ends of the first and second blades may be space apart and, in the open position, the proximal ends of the first and second blades may be closer together than in the closed position and the distal ends of the first and second blades may be farther apart than in the closed position. Another method may comprise inserting an expandable device, such as those described above, proximate the spine, inserting the blades into the body in a closed position such the distal ends of the blades may be positioned proximate the spine and the proximal ends of the blades may be positioned outside the body, wherein the distal ends of the blades may be positioned adjacent each other and the proximal ends of the blades may be spaced apart from each other, and moving the blades to an opened configuration, wherein the distal ends of the blades may be spaced apart from each other.

BRIEF DESCRIPTION OF THE DRAWINGS

The retractor and its method of use may be better understood by reference to the following drawings, wherein like references numerals represent like elements. The drawings are merely exemplary to illustrate certain features that may be used singularly or in combination with other features and, thus, the present invention should not be limited to the embodiments shown.

FIG. 1A is an perspective view of an exemplary embodiment of the device of the present invention in a closed configuration;

FIG. 1B is a front view of the device of FIG. 1A;

FIG. 2A is an perspective view of an exemplary embodiment of the device of FIG. 1A in an opened configuration;

FIG. 2B is a front view of the device of FIG. 2A;

FIG. 2C is a perspective back view of the device of FIG. 2A;

FIG. 2D is a top view of the device of FIG. 2A;

FIG. 2E is a side view of an embodiment of the device of FIG. 2A;

FIG. 3A is a front view of the device of the present invention in a closed configuration positioned in the body;

FIG. 3B is a perspective view of the device of FIG. 3A in a closed configuration positioned in the body;

FIG. 3C is a front view of the device of FIG. 3A in an opened configuration positioned in the body;

FIG. 3D is a perspective view of the device of FIG. 3A in an opened configuration positioned in the body;

FIG. 4C is a front view of the device of FIG. 4A in an opened configuration positioned in the body;

FIG. 4D is a perspective view of the device of FIG. 4A in an opened configuration positioned in the body;

FIG. 5A is an perspective view of the device of FIG. 1A with an exemplary actuating device;

FIG. 5B is a front view of the device of FIG. 5A;

FIG. 5C is a perspective back view of the device of FIG. 5A;

FIG. 5D is a top view of the device of FIG. 5A;

FIG. 5E is a side view of the device of FIG. 5A;

FIG. 6A is an perspective view of the device of FIG. 1A with an alternative exemplary actuating device;

FIG. 6B is a front view of the device of FIG. 6A;

FIG. 6C is a perspective back view of the device of FIG. 6A;

FIG. 6D is a top view of the device of FIG. 6A;

FIG. 6E is a side view of the device of FIG. 6A;

FIG. 7 is a perspective view of the device of FIG. 6A as it is being inserted into the body in a closed configuration;

FIG. 8 is a perspective view of the device of FIG. 6A positioned in the body in a closed configuration and rotated 90 degrees;

FIG. 9A is a perspective view of the device of FIG. 6A in the body in an opened configuration; and FIG. 9B is a front view of the device of FIG. 6A in the body in an opened configuration.

DETAILED DESCRIPTION

Figure 1E:
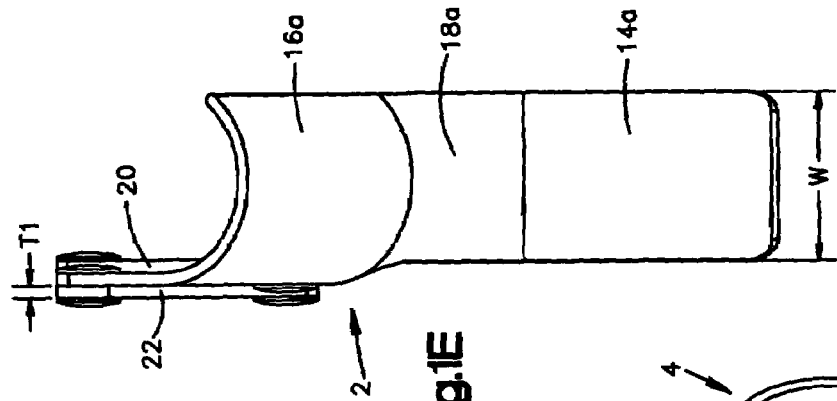
FIG. 1E is a side view of the device of FIG. 1A.

In general, the expandable access device described herein may be used to perform surgical procedures such as, for example, pedicle screw fixation, discectomies, facectomies, laminectomies and may be used for anterior, lateral, anteriolateral, posterior and posterio-lateral approaches to the lumbar, thoracic and cervical areas of the spine. The expandable access device may also be sized and configured to perform single or multi-level procedures. Although the expandable access device is described herein as being used in connection with spinal surgical procedures, one of ordinary skill in the art will readily appreciate that the device may be used in any other parts of the body to perform any surgical procedure. Thus, the location and/or surgical procedure is not intended to be limiting in any way. Moreover, while the device is described herein as being used to perform procedures on humans, the device may be sized and configured to perform procedures on animal subjects as well. Furthermore, it will be appreciated by those skilled in the art that one or more expandable access devices may be used to perform a procedure. For instance, in a bi-lateral procedure, a first expandable access device may be placed on one side of the spinous process and a second expandable access device may be placed on an opposite side of the spinous process.

As shown in FIG. 1A, the expandable access device 1 of the present invention may include a first blade 2 and a second blade 4, which may be joined together by a connection mechanism 6. Each blade may have a distal end 10a, 10b, a proximal end 12a, 12b, a first portion 14a, 14b positioned proximate the distal end 10a, 10b, a second portion 16a, 16b positioned proximate the proximal end 12a, 12b, and an intermediate portion 18a, 18b, which may be located between the first portion 14a, 16a and second portion 14b, 16b, respectively. It should, however, be understood that those of ordinary skill in the art will recognize many modifications and substitutions which may be made to various elements of the expandable access device.

The blades 2, 4 may be made of any suitable material, preferably biocompatible material, such as metal (e.g., stainless steel, titanium, aluminum and alloys thereof), plastic, ceramic, rubber, an alloy of two or more materials or a composite material (i.e., made up of two or more materials). Various factors may be considered when determining the material used to make the elements of the device 1, including but not limited to, for example, ability to withstand sterilization, ability to move tissue without deforming, weight, durability, resistance to staining, and the ability to grip the device 1, particularly with latex gloves. The blades 2, 4 and/or any other component of the expandable access device 1 may be radiolucent or radioopaque. In embodiments where the blades 2, 4 or other components may be radiolucent, radioopaque markers (not shown) may be incorporated into or attached to the blades 2, 4 or other components. The radioopaque markers may assist a surgeon in properly aligning the blades 2, 4 or other components relative to a patient's anatomy. One or both of the blades 2, 4 may be smooth, textured and/or may have holes or openings partially or completely therethrough. Incorporating holes or openings (not shown) into/through a blade 2, 4 may reduce pressure on surrounding tissue when the device 1 is in use and may provide other advantages as well (e.g., reducing the weight of the device 1).

Furthermore, the blades 2, 4 may be any shape or size and may be flat or may have a concave/convex shape as shown in FIG. 1A. For example, the blades 2, 4 may have a concave shape on the inner surface between the blades 2, 4 and/or a convex shape on the outer surface of the blades 2, 4. As an example, the width W of the blades 2, 4 may have a radius of curvature $R_B$ (FIG. 2D) of between about 5 mm and about 100 mm, more preferably, between about 7 mm and about 50 mm and, most preferably, between about 10 mm and about 30 mm. The curvature of the blades across their width W may result in opening O having a dimension D6. The radius of curvature $R_B$ and/or the way in which the connection mechanism 6 may move the blades 2, 4 relative to each other may dictate the minimum and maximum dimension of the opening O (i.e., the space through which surgical instruments may be inserted through the device 1) when the device 1 is in the opened and/or closed configuration. Alternatively, the blades 2, 4 may have an inner surface which may be flat and an outer surface which may be convex, an inner surface which may be concave and an outer surface which may be flat, an inner surface which may be flat and an outer surface which may be concave, or an inner surface which may be convex and an outer surface which may be flat.

In a preferred embodiment the blades may be non-straight. For example, as shown in FIG. 1B, the intermediate portion 18a, 18b may be bent such that an angle $\theta_a$, $\theta_b$ may be formed between the first portion 14a, 14b and the second portion 16a, 16b. The angle $\theta_a$, $\theta_b$ may be, for example, between about 100 degrees and about 170 degrees, more preferably, between about 110 degrees and about 150 degrees and, most preferably, between about 120 degrees and about 140 degrees. The angles $\theta_a$, $\theta_b$ may be the same or different. Those skilled in the art will appreciate that the angle $\theta$ may be chosen so that a surgeon may have a line of site LS1, LS2 (FIG. 2B) down the device 1 so that the surgeon may visualize the entire surgical site in the body at the surgical work level SWL (FIGS. 3A-4D). Alternatively, the blades 2,4 may be curved along their lengths and may have a radius of curvature $R_C$ of, for example, between about 1 mm and about 100 mm, more preferably, between about 10 mm and about 50 mm and, most preferably, between about 20 mm and about 30 mm. The radius of curvature $R_C$ and/or the way in which the connection mechanism 6 may move the blades 2, 4 relative to each other may dictate the size and/or may set up the relationship between the sizes of the openings O1 and O2. The angle and/or radius of curvature may also be chosen to provide a minimal opening at the facia level FL and/or skin level SL and a maximum space at the surgical work level SWL. In a preferred embodiment, the device may be configured and positioned in the body so as to provided a minimum opening at the facia level FL. Those skilled in the art will appreciate that providing an expandable access device which may allow for a minimal opening at the facia level FL may be desirable since the facia is tough tissue and may be difficult to maneuver. Furthermore, the first and second blades 2, 4 may have a length L (FIG. 1B), for example, between about 30 mm and about 300 mm, more preferably, between about 50 mm and about 200 mm and, most preferably, between about 70 mm and about 150 mm. The first and second blades 2, 4 may have a width W (FIG. 1E), for example, between about 5 mm and about 250 mm, more preferably, between about 10 mm and about 100 mm and, most preferably, between about 15 mm and about 50 mm. The first and second blades 2, 4 may also have a thickness T (FIG. 1D), for example, between about 0.1 mm and about 10 mm, more preferably, between about 0.3 mm and about 5 mm and, most preferably, between about 0.5 mm and about 2.5 mm.

Figure 1D:
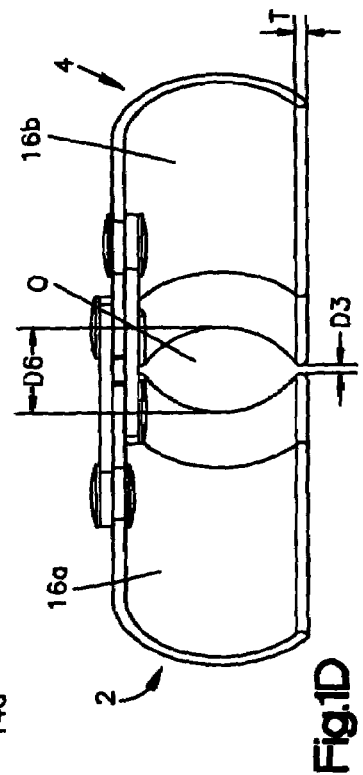
FIG. 1D is a top view of the device of FIG. 1A.

As shown in FIG. 1D, when the device 1 is in the closed configuration, the distance D3 between the first portions 14a, 14b of the blades 2, 4, respectively, may be between about 0 mm and about 10 mm, more preferably, between about 0 mm and about 5 mm and, most preferably, between about 0 mm and about 1 mm. Moreover, an internal opening O may be formed between portions 14a, 14b, which may have a dimension D6 of, for example, between about 0 mm (e.g., when the blades 2, 4 are flat) and about 100 mm, more preferably, between about 5 mm and about 50 mm and, most preferably, between about 10 mm and about 20 mm. The size of dimension D6 may depend on the shape of the blades 2, 4.

As shown in FIG. 1B, in the closed configuration the blades 2, 4 of the device 1 may have an outer dimension OD of, for example, between about 0.2 mm and about 120 mm, more preferably, between about 5 mm and about 30 mm and, most preferably, between about 10 mm and about 20 mm. Accordingly, the dimension of the opening DSL (FIG. 3B) created at the skin level SL and/or an opening created at the facia level FL when the device 1 is inserted into the body in the closed configuration may be substantially the same as the dimension OD.

Figure 1C:
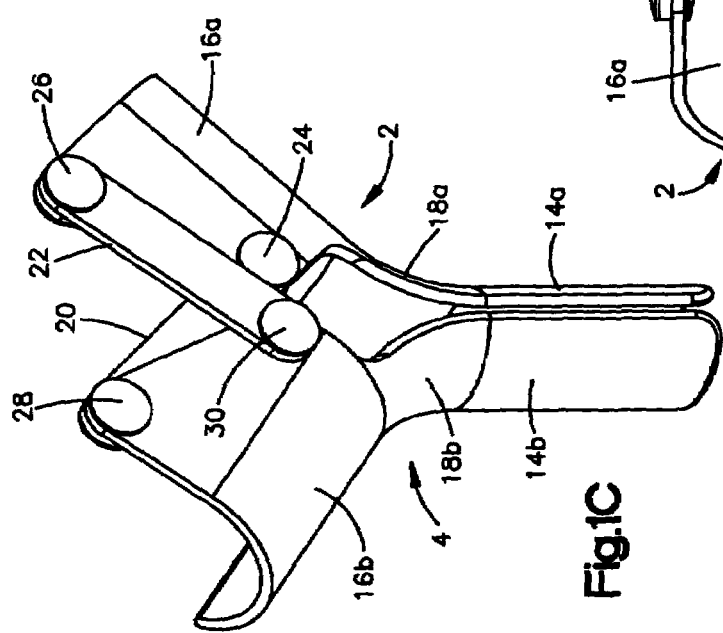
FIG. 1C is a perspective back view of the device of FIG. 1A.

The connection mechanism 6 may be operable connected to the first and second blades 2, 4 such that the blades 2, 4 may be moved towards or away from each other and pivot with respect to each other. The connection mechanism 6 may be made of a first elongated member 20 having a first end 20a and a second end 20b, and a second elongated member 22 having a first end 22a and a second end 22b. The elongated members 20, 22 may be any shape such as, for example, flat (e.g., plate) or round (e.g., rod). The first ends 20a, 22a of each elongated member 20, 22 may be operably connected to the first blade 2 and the second ends 20b, 22b of each elongated member 20, 22 may be operable connected to the second blade 4. The first end 20a of the first elongated member 20 may have a first pivot point 24 and the first end 22a of the second elongated member 22 may have a second pivot point 26. The second end 20b of the first elongated member 20 may have a third pivot point 28 and the second end 22b of the second elongated member 22 may have a fourth pivot point 30. Moreover, the first and second elongated members 20, 22 may be oriented in a criss-cross configuration such as shown in FIGS. 1A-1C. While the embodiments illustrate the pivot points 24, 26 and 28, 30, respectively, being equidistant from the axis A-A (FIG. 3A), it will be appreciated by those skilled in the art that the pivot points 24, 26 and 28, 30, respectively, may be positioned in a non-equidistant relationship from axis A-A. Such a non-equidistant placement may result in first and second blades 2, 4 moving in a non-symmetrical manner.

Similar to blades 2, 4, the elongated member 20, 22 may be made of any suitable material, preferably biocompatible material, such as metal (e.g., stainless steel, titanium, aluminum or alloys thereof), plastic, ceramic, rubber, an alloy of two or more materials or a composite material (i.e., made up of two or more materials). It will be appreciated by those skilled in the art that the connection mechanism 6 may be any structure or configuration which enables the blades 2, 4 to move laterally as well as pivotally with respect to each other.

The first and second elongated members 20, 22 may have a length L1 (FIG. 1B) from pivot point to pivot point (e.g., pivot point 26 to pivot point 30, pivot point 24 to pivot point 28), for example, between about 20 mm and about 150 mm, more preferably, between about 25 mm and about 100 mm and, most preferably, between about 30 mm and about 50 mm. Those skilled in the art will recognized that the elongated members 20, 22 may be the same or different lengths. The pivot points on the same blade (e.g., between pivot point 24 and 26 or between pivot point 28 and 30) may have a distance D7 therebetween of, for example, between about 5 mm and about 100 mm, more preferably, between about 10 mm and about 80 mm and, most preferably, between about 20 mm and about 50 mm. The first and second elongated members 20, 22 may also have a dimension or thickness T1 (FIG. 1E), for example, between about 0.1 mm and about 5 mm, more preferably, between about 0.2 mm and about 3 mm and, most preferably, between about 0.5 mm and about 2.5 mm. In the closed configuration, shown in FIG. 1B, the first and fourth pivot points 24, 30 may be a distance D1 apart, for example, between about 1 mm and about 40 mm, more preferably, between about 5 mm and about 30 mm and, most preferably, between about 10 mm and about 20 mm. Moreover, in the closed position, the second and third pivot point 26, 28 may be a distance D2 apart, for example, between about 15 mm and about 150 mm, more preferably, between about 20 mm and about 100 mm and, most preferably, between about 30 mm and about 50 mm.

In the opened configuration, shown in FIG. 2B, the first and fourth pivot point 24, 30 may be a distance D1 apart, for example, between about 10 mm and about 60 mm, more preferably, between about 15 mm and about 40 mm and, most preferably, between about 20 mm and about 30 mm. Moreover, the second and third pivot point 26, 28 may be a distance D2 apart, for example, between about 5 mm and about 50 mm, more preferably, between about 10 mm and about 30 mm and, most preferably, between about 15 mm and about 25 mm.

Figure 4B:
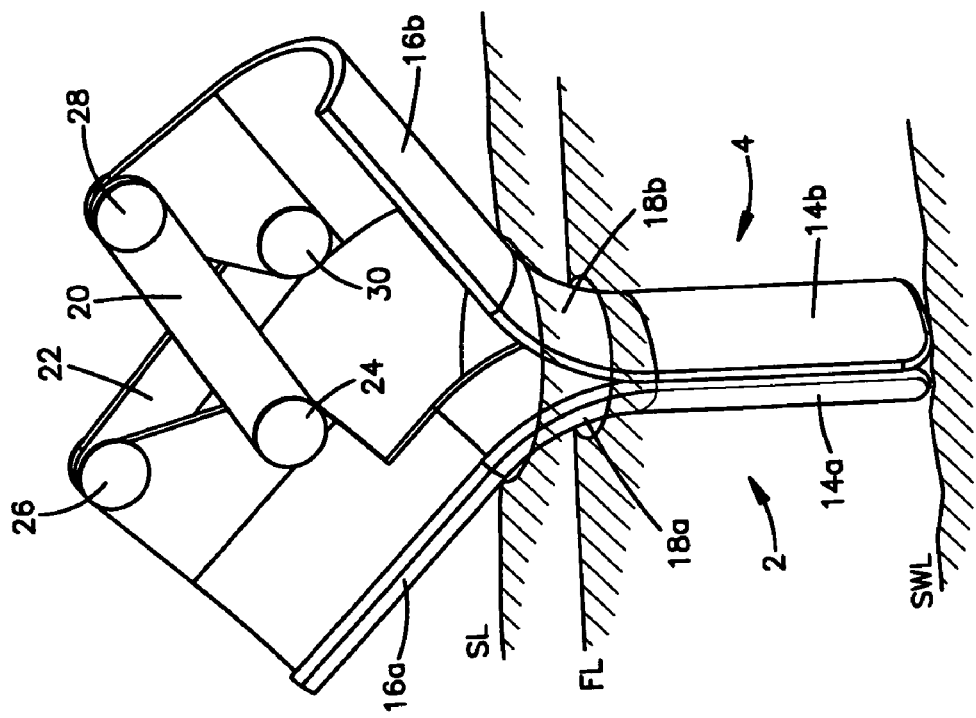
FIG. 4B is a perspective view of the device of FIG. 4A in a closed configuration positioned in the body.
Figure 4A:
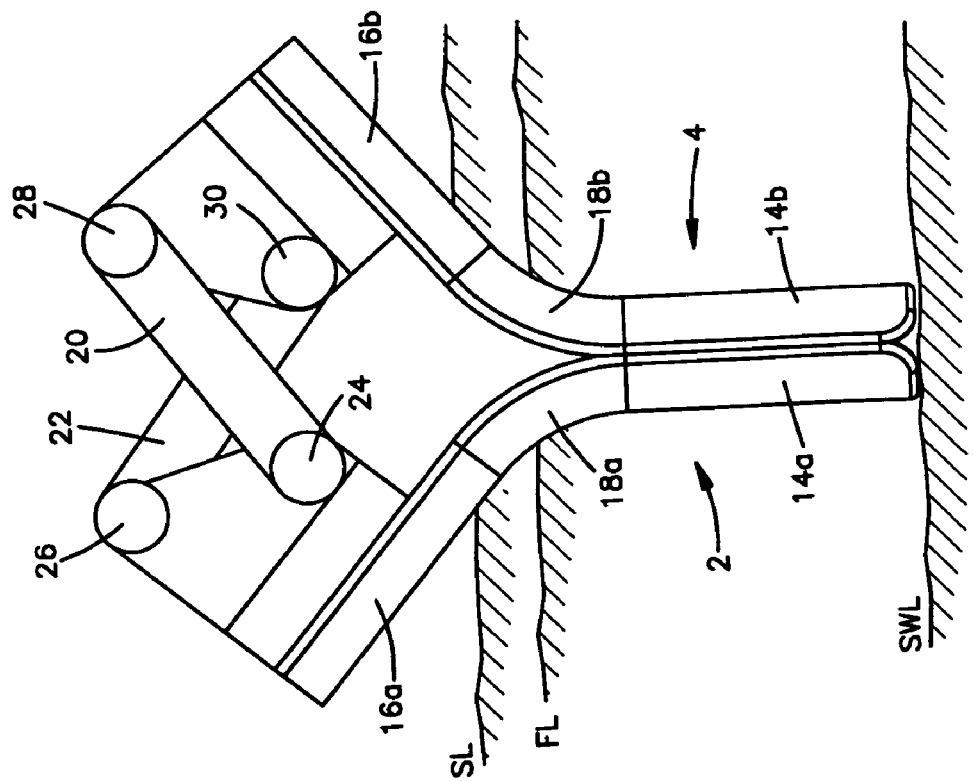
FIG. 4A is a front view of an alternative embodiment of the device of the present invention in a closed configuration positioned in the body.

The construction of the connection mechanism 6 may determine the distance between the blades 2, 4 as well as the size of the opening in the skin and tissue when the device 1 is in the opened configuration. For example, as shown in FIGS. 2D, 3C and 4C, the distance D5 between the intermediate portions 18a, 18b of the blades 2, 4, respectively, may be between about 5 mm and about 80 mm, more preferably, between about 10 mm and about 60 mm and, most preferably, between about 20 mm and about 40 mm. Moreover, as shown in FIG. 2D, an internal opening O may be formed between portions 18a, 18b, which may have a dimension D4 of, for example, between about 5 mm and about 100 mm, more preferably, between about 10 mm and about 80 mm and, most preferably, between about 20 mm and about 50 mm. As illustrate in FIG. 3D, in the opened configuration the device 1 may create an opening O1 in the skin at the skin level SL which may have a major dimension MSL1 of, for example, between about 5 mm and about 110 mm, more preferably, between about 10 mm and about 80 mm and, most preferably, between about 20 mm and about 50 mm as well as a minor dimension MSL2 of, for example, between about 5 mm and about 250 mm, more preferably, between about 10 mm and about 100 mm and, most preferably, between about 15 mm and about 50 mm. Furthermore, as shown in FIG. 3D, in the opened configuration the device 1 may create an opening O2 proximate a surgical work level SWL, which may have a major dimension MD1 of, for example, between about 20 mm and about 250 mm, more preferably, between about 30 mm and about 150 mm and, most preferably, between about 40 mm and about 100 mm, as well as a minor dimension MD2 of, for example, between about 5 mm and about 250 mm, more preferably, between about 10 mm and about 100 mm and, most preferably, between about 15 mm and about 50 mm.

Various factors that may control the distances between the portions of the blades and may include, for example, length of the elongated members 20, 22 as well as the location where pivot points 24, 26, 28 and 30 are attached to the blades 2, 4. Increasing or decreasing the length of the elongated member 20, 22 and/or increasing or decreasing the distance D7 (while keeping the pivot points 26 and 28 stationary), may affect the distance D5 and/or major dimension MD1. For example, as the length L1 of the elongated members 20, 22 increases from the length shown in FIG. 3C to the length shown in FIG. 4C, the distance D5 and/or major dimension MD1 may also increase. Moreover, by maintaining the position of pivot points 26 and/or 28 and decreasing the distance D7 (and/or the length of members 20, 22), such that the pivot points 24 and 26 and/or 28 and 30 may be closer to each other, may result in an increase in the distance D5 and/or major dimension MD1 as compared to the embodiment of FIG. 3C or 4C. Those skilled in the art will appreciate that the length L1 of the elongate members 20, 22 and/or the distance D7 between pivot points 24 and 26 and/or 28 and 30 (keeping the pivot points 26 and 28 stationary) may be chosen so that a surgeon may have a line of site LS1, LS2 (FIG. 2B) down the device 1 so that the surgeon may visualize the entire surgical site in the body at the surgical work level SWL. The length L1 and distance D7 may also be chosen to provide a minimal opening at the skin level SL and/or facia level FL and a maximum opening at the surgical work level SWL. Furthermore, decreasing and/or increasing the distance D7 (and/or the length of members 20, 22) may decrease and/or increase the rate at which the blades 2 and 4 move together or part with respect to each other.

The configuration of the expandable access device 1 may allow for a step-less opening such that the blades 2, 4 of the device 1 may be separated any distance with respect to each other (i.e., the device 1 does not have predetermined distance(s) to which the blades 2, 4 may be opened and locked). For example, such a feature may enable a surgeon to use a single device to perform a one, two or three level procedure on the spine through an opening of any size. The device 1 may be used to form a first opening to perform a one level procedure, a second opening (e.g., greater in dimension than the first opening) to perform a two level procedure and/or a third opening (e.g., greater in dimension than the second opening) to perform a three level procedure. In other embodiments, an actuating device or other instrument may be operably connected to the blades so that the blades may be only opened to one or more fixed positions (to create predetermined sized openings into the body) and locked in position.

An actuating device may be attached to the pivot points 20, 22, the blades 2, 4 or anywhere on the connecting mechanism 6. For example, the actuating device may be connected at an angle, preferably perpendicular, to the connection mechanism 6. In some embodiments, the actuating device may be connected by a pivot to the connection mechanism 6. The actuating device may be used to operate the connection mechanism 6. In a preferred embodiment, the actuating device may be any device which may create linear movement. In one embodiment, as shown in FIGS. 5A-5E, the actuating device may be a scissor-type mechanism 32, which may have a pair of handles 34 and 36 which may pivot with respect to each other (i.e., operated in a scissor-type manner). The handles 34 and 36 may be operably connected to the pivot points 26 and 28, respectively, and/or to the first and second blades 2 and 4, respectively. The scissor-type mechanism 32 may also incorporate a locking mechanism (not shown) to hold the blades 2, 4 in a fixed orientation relative to each other.

In another embodiment, as illustrated in FIGS. 6A-6E, the actuating device may be a ratchet mechanism 46. In particular, as shown in FIGS. 6A and 6C, the ratchet mechanism 46 may have a first connection portion 48 which may be operably associated with the first blade 2, a second connecting portion 50 which may be operably associated with the second blade 4, and a longitudinal member 52 joining the first and second connecting portions 48, 50. The longitudinal member 52 may be fixedly attached to the second connecting portion 50 and may be moveably connected to the first connecting portion 48. The longitudinal member 52 may have a plurality of teeth 54 which may be engaged by a cam (not shown) positioned within a housing 56 of the first connecting portion 48. The cam may have teeth (not shown) for engaging the teeth 54 of the member 52 and may be connected to a knob 58. Accordingly, rotation of knob 58 may result in rotation of the cam, thus causing the longitudinal member 52 to move with respect to the first connecting portion 48.

In use, rotation of the knob 58 in a first direction (e.g., counterclockwise) may result in the connecting portions 48, 50 moving towards each other and, consequently, may result in the blades 2, 4 moving with respect to each other so that the first portion 14a, 14b of the blades 2, 4 may move away from each other (i.e., the blades 2, 4 are moved towards an opened configuration). Conversely, rotation of the knob 58 in a second direction (e.g., clockwise) may result in the connecting portions 48, 50 moving away from each other and, consequently, may result in the blades 2, 4 moving with respect to each other so that the first portions 14a, 14b of the blades 2, 4 may move together (i.e., the blades 2, 4 are moved towards a closed configuration). The ratchet mechanism 46 may also incorporate a locking mechanism to hold the blades 2, 4 as well as the first and second connecting portions 48, 50 in a fixed orientation relative to each other. In addition, the locking mechanism 46 may also prevent movement of the first connecting portion 48 relative to the longitudinal member 52 if the knob 58 is turn. For example, the first connecting portion 48 may have a latch 60 which may be moveable to be selectively positioned in between the teeth 54. Such a construction may prevent unintended movement of the blades 2, 4 (e.g., closing of the blades 2, 4), connecting portion 48 and/or member 52.

Those skilled in the art will appreciated that at least a portion of the actuating device may be detachable from at least one of the first and second blades 2, 4. The actuating device may be completely or partially detached from the blades 2, 4. For example, as shown in FIGS. 5A and 5C, the handles 34, 36 may be sized and configured so that a surgeon can disengage and remove the actuating device 32 from the expandable access device 1. In such an embodiment, the handles 32, 34 may be disengaged at the place where the handles 32, 34 connect to the pivot points 26, 28 and/or the blades 2, 4. Alternatively, as shown in FIGS. 5A, and 5C, the handles 32, 34 may be disengaged at location 38 from distal handle portions 42, 44, respectively. The handles 34, 36 may be attached at distal handle portions 42, 44 by screws, pegs, pins, adhesive, bolts, etc. It should be noted, however, that in an embodiment where the actuating device 32 may be removed from the device 1, the expandable access device 1 may incorporate a device/features (or a device is attached thereto) for maintaining the orientation and space between blades 2, 4. Those skilled in the art will appreciate that the actuating device 46 of FIGS. 6A-6E may also be configured to disengage from the expandable access device 1 in the same manner as actuating device 32 provided that the expandable access device 1 incorporates a device/features (or a device is attached thereto) for maintaining the orientation and space between blades 2, 4. Such a construction may allow the surgeon to remove the actuating device 32, 46 during surgery (i.e., once the expandable access device 1 has been positioned in a desired location in the body and expanded) and may provide the surgeon with an unencumbered access to the device 1 during surgery (i.e., so that the actuating device 32, 46 does not get in the way of the surgeon during surgery). After surgery is complete, the surgeon may reattach the actuating device 32, 46 to the blades 2, 4, thereby enabling the surgeon to move the bladed 2, 4 to a closed configuration and remove the device 1 from the body.

It should be noted, however, that the first and second blades 2, 4 may be moved without the use of an actuating device (e.g., actuating device 32, 46). In such an embodiment, a surgeon may grasp the first blade 2 (e.g., at the proximal end 12*a*) and/or the second blade 4 (e.g., at the proximal end 12*b*) and may move the blades 2, 4 apart and/or together. In one embodiment, the first and/or second blades 2, 4 may have a textured (e.g., knurled) surface or may be shaped to enhance a user's grip, particularly when latex gloves are worn.

The combination of the connection mechanism and a actuating device which may impart linear movement may result in the first and second blades moving apart from each other while, at the same time, pivoting with respect to each other. The expandable access device 1 may have a first or closed configuration, where the first portions of the blades are adjacent and/or parallel to each other. In the first or closed configuration, the second portions of the blades may be spaced apart and/or at an angle with respect to each other. The device may also have a second or opened configuration, where the first portions of the blades are spaced apart and/or at an angle with respect to each other.

It should also be noted that the device 1 may be configured so that surgical instruments may be attached thereto (e.g., a light, nerve root retractor, camera, etc). Such devices may provided extra visibility or functionality to the user and may allow the freeing of the users hands for other uses.

In use, the blades 2, 4 may be inserted in the first or closed configuration through an incision in the skin and facia. The incision may be in made in the same direction of the muscle fibers in the back (e.g., parallel to the spine). In one preferred embodiment, as shown in FIG. 7, the blades 2, 4 may be inserted into the body in a closed configuration and the width W (FIG. 1E) of the blades 2, 4 may be parallel to the spine S. The blades 2, 4 may be inserted into the body through the skin level SL and facia level FL until the intermediate portion 18*a*, 18*b* of the blades 2, 4 may be positioned in and/or proximate the skin/facia level SL, FL and the distal end of the blades 2, 4 are proximate the surgical site (e.g., proximate the vertebrae). For example, the first and second blades 2, 4 may be inserted into the body such that the length L2 (FIG. 1B) from the distal most portion 10*a*, 10*b* of the blades 2, 4 to the point on the blades 2, 4 where the blades 2, 4 exit the skin level SL and/or facia level FL may be between about 15 mm and about 150 mm, more preferably, between about 20 mm and about 100 mm and, most preferably, between about 25 mm and about 50 mm. Once the blades 2, 4 are positioned at a desired depth in the body, a surgeon may rotate the device 1 so that the blades 2, 4 may be position by the spine S as shown in FIG. 8. For example, the surgeon may rotate the blades 2, 4 (e.g., about 90 degrees) so that the blades 2, 4 may be at an angle with respect to the spine S (e.g., the width W of the blades 2, 4 may be approximately perpendicular to the spine S). Thereafter, as shown in FIGS. 9A and 9B, the surgeon may move the actuating device so that the blades 2, 4 may be spread apart and pivot with respect to each other (i.e., moved to an opened configuration). In a preferred embodiment, as illustrated in FIG. 9B, the smallest portion of the device 1 in the opened position may be located in the facia level FL. In this way, a surgeon only has to move/stretch the tough facia a minimal amount. The spreading and pivoting of the blades 2, 4 may spread tissue. It will be appreciated by those skilled in the art that the blades 2, 4 may be moved apart in increments depending on the requirements of a procedure. Thereafter, a surgical procedure (e.g., a single or multi-level procedure) may be performed through the expandable access device 1. Once the procedure is complete, a surgeon may move the actuating device so that the blades 2, 4 move towards each other (i.e., moved to a closed configuration). The device 1 may then be removed from the body. Alternatively, the device 1 may be, once again, rotated (e.g., 90 degrees) so that the width W of the blades 2, 4 may align with the initial incision. The device 1 may then be removed from the body.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. An expandable access device, comprising:
a first blade having a distal end and proximal end, the first blade comprises a first portion, a second portion and an intermediate portion in between the first and second portions, wherein the intermediate portion is bent such that the first and second portions are angled with respect to each other;
a second blade having a distal end and a proximal end, the second blade comprises a first portion, a second portion and an intermediate portion in between the first and second portions of the second blade, the second blade being operably connected to the first blade;
a first elongated member having a first end and a second end, wherein the first end is connected to the first blade at a first pivot point and the second end is connected to the second blade at a second pivot point; and
a second elongated member having a first end and a second end, wherein the first end is connected to the first blade at a third pivot point and the second end is connected to the second blade at a fourth pivot point,
wherein the distal end of the first blade is moveable with respect to the distal end of the second blade; and
wherein the device has an opened configuration and closed configuration, wherein the intermediate portions of the first and second blades are closer to each other than the distal most ends of the first and second blades when the device is in the opened configuration.

2. The device of claim 1, wherein the intermediate portion of the second blade is bent such that the first and second portions of the second blade are angled with respect to each other.

3. The device of claim 1, further comprising an actuating device operable connected to the first and second blades.

4. The device of claim 3, wherein the actuating device comprises a pair of handles.

5. The device of claim 3, wherein the actuating device comprises a ratchet mechanism.

6. The device of claim 3, wherein the actuating device is sized and configured to create linear movement of the first and second blades relative to each other.

7. The device of claim 3, wherein the actuating device is operable connected to the proximal end of the first and second blades.

8. An expandable access device, comprising:
a first blade having a distal end and proximal end, the first blade comprises a first portion, a second portion and an intermediate portion in between the first and second portions, wherein the first and second portions are at an angle with respect to each other;
a second blade having a distal end and a proximal end, the second blade being operably connected to the first blade, the second blade comprises a first portion, a second portion and an intermediate portion in between the first and second portions of the second blade, wherein the first and second portions of the second blade are at an angle with respect to each other;
a first elongated member having a first end and a second end, wherein the first end is connected to the first blade at a first pivot point and the second end is connected to the second blade at a second pivot point; and
a second elongated member having a first end and a second end, wherein the first end is connected to the first blade at a third pivot point and the second end is connected to the second blade at a fourth pivot point,
wherein the distal end of the first blade is moveable with respect to the distal end of the second blade;
wherein the device has an opened configuration and closed configuration, wherein the intermediate portions of the first and second blades are closer to each other than the distal most ends of the first and second blades when the device is in the opened configuration;
wherein the access device further comprises an actuating device operable connected to the first and second blades, the actuating device being operably connected to the first blade at the third pivot point and the second blade at the second pivot point.

9. The device of claim 8, wherein the second pivot point is proximal the first pivot point and the fourth pivot point is distal the third pivot point such that the first and second elongated members are in a criss-cross configuration.

10. The device of claim 9, wherein the first and second elongated members have a length between about 20 mm and about 150 mm.

11. The device of claim 1, wherein the first and second blades have a length between about 30 mm and about 300 mm.

12. The device of claim 11, wherein the first and second blades have a width between about 5 mm and about 250 mm.

13. The device of claim 12, wherein the first and second blades have a thickness between about 0.1 mm and about 10 mm.

14. The device of claim 1, wherein at least one of the first and second blades has at least one of a textured surface and an opening therethrough.

* * * * *